(12) United States Patent
Takagi

(10) Patent No.: US 9,816,994 B2
(45) Date of Patent: *Nov. 14, 2017

(54) METHOD FOR TREATING A BLOOD COMPONENT CONTAINING SAMPLE

(71) Applicant: ARKRAY, Inc., Kyoto (JP)

(72) Inventor: Hidenori Takagi, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/161,170

(22) Filed: May 20, 2016

(65) Prior Publication Data

US 2016/0266123 A1    Sep. 15, 2016

Related U.S. Application Data

(62) Division of application No. 13/920,142, filed on Jun. 18, 2013, now Pat. No. 9,429,501.

(30) Foreign Application Priority Data

Jun. 20, 2012 (JP) ................. 2012-139051
Jun. 17, 2013 (JP) ................. 2013-126403

(51) Int. Cl.

| | | |
|---|---|---|
| *C12Q 1/02* | (2006.01) | |
| *G01N 33/574* | (2006.01) | |
| *G01N 1/28* | (2006.01) | |
| *G01N 33/50* | (2006.01) | |
| *C08G 65/26* | (2006.01) | |
| *G01N 15/00* | (2006.01) | |
| *G01N 15/14* | (2006.01) | |
| *G01N 15/10* | (2006.01) | |

(52) U.S. Cl.
CPC .......... *G01N 33/574* (2013.01); *C08G 65/26* (2013.01); *G01N 1/28* (2013.01); *G01N 15/14* (2013.01); *G01N 33/5002* (2013.01); *G01N 33/5005* (2013.01); *G01N 15/147* (2013.01); *G01N 2015/008* (2013.01); *G01N 2015/0065* (2013.01); *G01N 2015/1006* (2013.01); *G01N 2015/1486* (2013.01)

(58) Field of Classification Search
None
See application file for complete search history.

(56) References Cited

U.S. PATENT DOCUMENTS

| | | |
|---|---|---|
| 5,389,549 A | 2/1995 | Hamaguchi et al. |
| 5,476,587 A | 12/1995 | Kuroki et al. |
| 5,707,520 A | 1/1998 | Kuroki et al. |
| 6,365,362 B1 | 4/2002 | Terstappen et al. |
| 2003/0219850 A1 | 11/2003 | Tsuji et al. |
| 2004/0067575 A1 | 4/2004 | Hanaoka et al. |
| 2006/0223137 A1 | 10/2006 | Yoshida et al. |
| 2010/0151509 A1 | 6/2010 | Ting et al. |
| 2011/0027788 A1 | 2/2011 | Zhao et al. |
| 2011/0250588 A1 | 10/2011 | Sato et al. |

FOREIGN PATENT DOCUMENTS

| | | |
|---|---|---|
| EP | 0316453 A1 | 5/1989 |
| EP | 1406088 A2 | 4/2004 |
| EP | 1715345 A1 | 10/2006 |
| EP | 2495565 A1 | 9/2012 |
| JP | 2004-141150 A | 5/2004 |
| JP | 3834326 B | 1/2005 |
| JP | 2006-304774 A | 11/2006 |
| JP | 2007-178193 A | 7/2007 |
| JP | 2010-075073 A | 4/2010 |
| WO | 95/20429 A1 | 8/1995 |
| WO | 2004/056978 A1 | 7/2004 |
| WO | 2005/043121 A2 | 5/2005 |
| WO | 2006/078994 A2 | 7/2006 |
| WO | 2006/116327 A1 | 11/2006 |
| WO | 2008/057437 A2 | 5/2008 |
| WO | 2008/155398 A1 | 12/2008 |
| WO | 2010/071114 A1 | 6/2010 |

OTHER PUBLICATIONS

Dotan et al., "Circulating Tumor Cells: Evolving Evidence and Future Challenges," Oncologist, 14: 1070-1082 (2009).
Extended European Search Report issued in related European Patent Application No. 13173100.2 dated Oct. 8, 2013.
Office Action issued in corresponding European Patent Application No. 13173100.2 dated Jun. 7, 2017.
Shearman et al., "A lyotropic inverse ribbon phase in a branched-chain polyoxyethylene surfactant: pressure effects," Soft Matter, 7: 4386-4390 (2011).

*Primary Examiner* — Thomas J Visone
(74) *Attorney, Agent, or Firm* — Morgan, Lewis & Bockius LLP

(57) ABSTRACT

Provided is a treatment method for damaging an erythrocyte and a leukocyte while suppressing damage to cells other than blood cells present in blood. In an embodiment, the disclosure relates to a method for treating a sample containing blood components, the method including mixing a sample containing blood components with a surfactant A, where the surfactant A is a nonionic surfactant represented by General formula $R^1-O-(EO)n-R^2$ (I).

3 Claims, 7 Drawing Sheets

No treatment with surfactant mixture

Treated with surfactant mixture

Example 11

Comparative Example 11

Example 12

Comparative Example 12

METHOD FOR TREATING A BLOOD COMPONENT CONTAINING SAMPLE

CROSS REFERENCE TO RELATED APPLICATIONS

The disclosure is based upon and claims priority from JP Application Serial Nos. 2012-139051 and 2013-126403, the disclosures of which are hereby incorporated by reference herein in their entireties.

TECHNICAL FIELD

The disclosure relates to a method for treating a blood containing sample, a method for separating a rare cell and a nucleic acid in a blood containing sample, a CTC number measurement method and a reagent kit.

BACKGROUND

Although cell components of blood include an erythrocyte, a leukocyte and a blood platelet, on rare occasion, a cell other than these cells may exist in the blood. An example thereof is a circulating tumor cell (CTC). It is considered that metastasis of cancer occurs since a cancer cell is conveyed through blood vessels or lymph vessels to any other site in the body and proliferates there. It has been reported that the number of CTCs (circulating tumor cells) in the blood correlate to the possibility of metastasis and prognosis, and thus it has been known that the number of CTCs in blood and a nucleic acid of a CTC are measured for providing a guideline for prediction or decision in diagnosis, prognostication, and a therapeutic effect of cancer (in particular, metastatic cancers such as breast cancer) (see *Circulating Tumor Cells; Evolving Evidence and Future Challenges*, The Oncologist 2009; 14; 1070-1082).

Examples of techniques for separating and detecting CTCs in blood include: a method of capturing and separating CTCs in blood by use of an antibody with respect to a CTC specific surface antigen (see JP 3834326 and JP 2007-178193 A); a separation method using adhesion (see WO 2005/043121 and WO 2006/078994); a separation method using a density gradient (see JP 2010-075073 A and WO 95/20429); a separation method using a filter (see WO 2006/116327 and WO 2008/155398); a method of measuring the telomerase activity of a CTC (see WO 2010/071114); a separation method through hemolysis by using a hypotonic solution (see WO 2004/056978); and a method utilizing flow cytometry (see WO 2008/057437). For detecting, quantifying and counting the object separated, measurement of a nucleic acid is generally carried out by utilizing PCR or any substance having affinity to a CTC; optical CTC measurements are carried out as a combination of an antigen and/or a fluorescent pigment.

SUMMARY

In an embodiment, the disclosure relates to a method for treating a sample containing blood components. A sample containing blood components and a liquid containing a surfactant A are mixed with each other. In the method, no fixation agent is used, and the surfactant A is a nonionic surfactant represented by General formula (I) below.

In the formula (I), $R^1$ is a hydrocarbon group having a branched chain and having a carbon number in the range of 12 to 40, EO is an oxyethylene group, n is an average addition mole number in the range of 23 to 50, and $R^2$ is a hydrogen atom or a hydrocarbon group having a carbon number in the range of 1 to 3.

In another embodiment, the disclosure relates to a method for treating a sample containing blood components. The method includes mixing a sample containing blood components with a liquid containing a surfactant A and a surfactant B, or with a liquid containing the surfactant A and a liquid containing the surfactant B. Here, the surfactant A is a nonionic surfactant represented by General formula (I) below, and the surfactant B has a lytic property with respect to an erythrocyte higher than the corresponding lytic property of the surfactant A.

$$R^1\text{—O-(EO)}n\text{-}R^2 \qquad (I)$$

In the formula (I), $R^1$ is a hydrocarbon group having a branched chain and having a carbon number in the range of 12 to 40, EO is an oxyethylene group, n is an average addition mole number in the range of 23 to 50, and $R^2$ is a hydrogen atom or a hydrocarbon group having a carbon number in the range of 1 to 3.

In another embodiment, the disclosure relates to a method for separating or detecting a rare cell or a nucleic acid in a sample containing blood components. Here, the method includes treating a sample containing blood components by any of the treatment methods according to the disclosure, and separating or detecting a rare cell or a nucleic acid from the treated sample.

In another embodiment, the disclosure relates to a method for measuring the number of CTCs or measuring a nucleic acid of a CTC in a sample containing blood components. Here, the method includes treating a sample containing blood components by the treatment methods according to the disclosure, or separating/detecting a rare cell or a nucleic acid from a sample containing blood components by the separation/detection methods according to the disclosure.

In another embodiment, the disclosure relates to a method for assaying a rare cell in a sample containing blood components. Here, the method includes treating a sample containing blood components by the treatment methods according to the disclosure, and subsequently assaying by a method including an observation of movements of the cell or an activity measurement.

In another embodiment, the disclosure relates to a reagent kit including the surfactant A and/or the surfactant B to be used for the treatment methods according to the disclosure, the separation/detection methods according to the disclosure, the methods for measuring a CTC number or a CTC nucleic acid according to the disclosure, and/or the assaying methods according to the disclosure.

BRIEF DESCRIPTION OF THE DRAWINGS

in FIG. 4A the sample

Figure 4A:
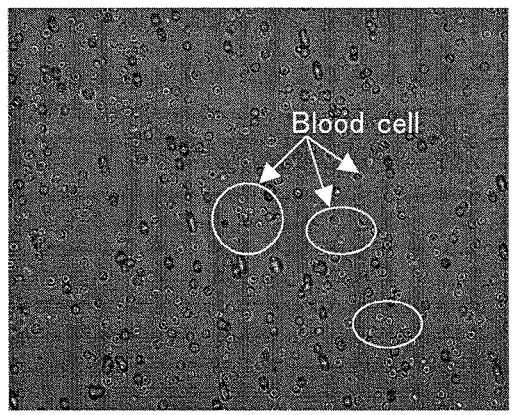
FIG. 4A and FIG. 4B is composed of microscopic photographs showing filtered samples.
Figure 4B:
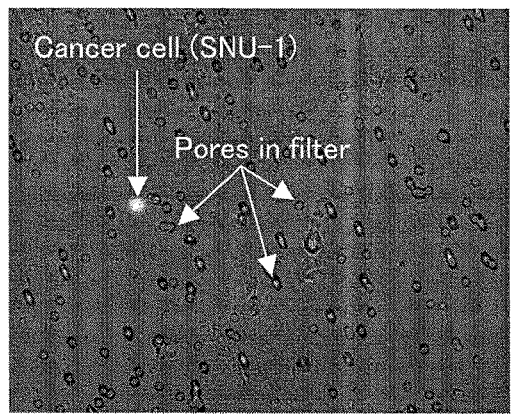

has not been treated with a surfactant mixture, and in FIG. 4B the sample has been treated with a surfactant mixture.

Figure 5:
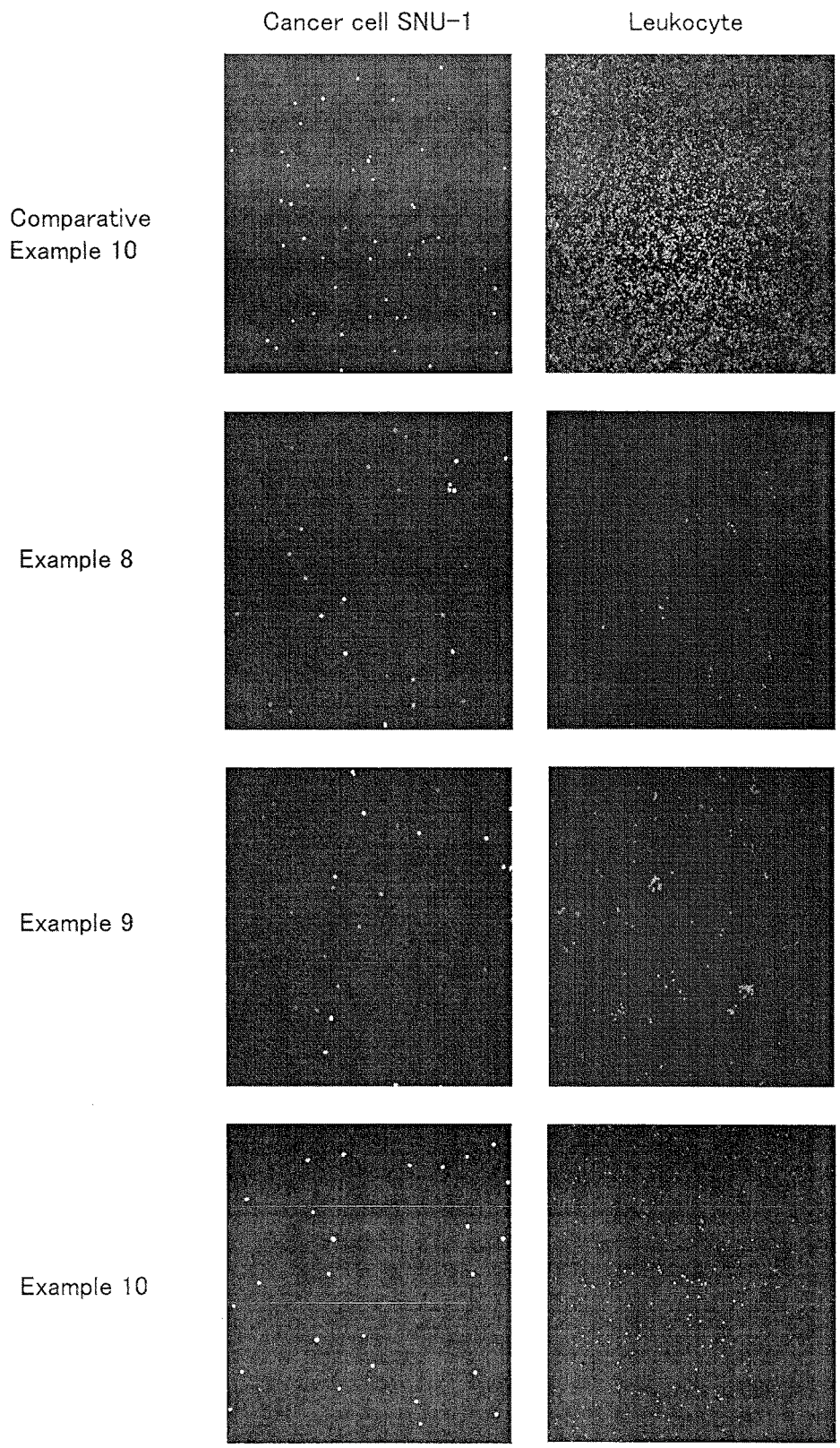

FIG. 5 shows the result of a fluorescence microscopic observation after treatment with a surfactant mixture with respect to a blood sample that includes cancer cells (SNU-1) stained with green fluorescence and leukocytes stained with blue fluorescence.

Figure 6A:
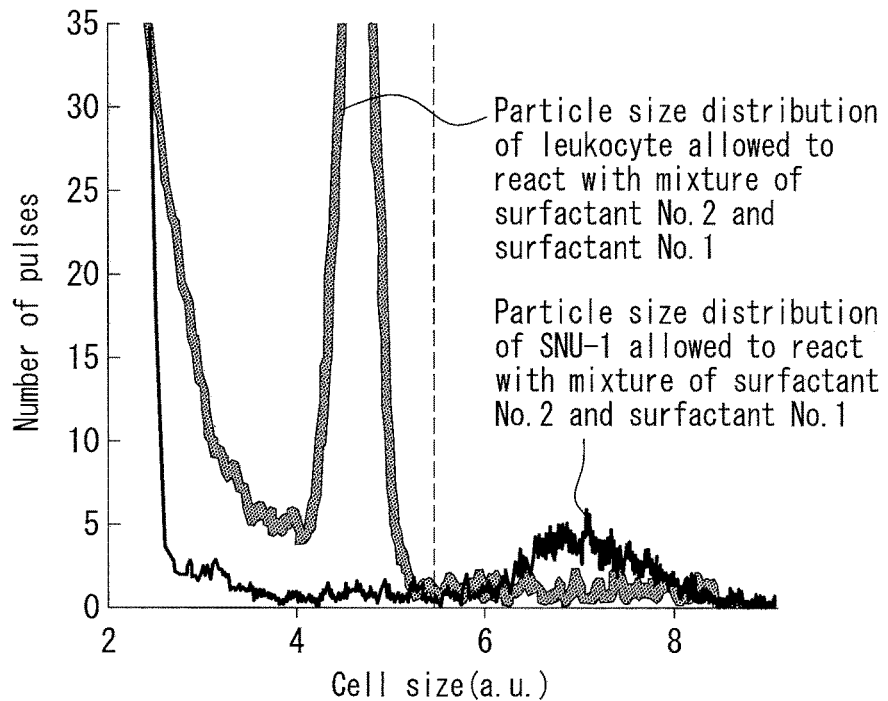
Figure 6B:
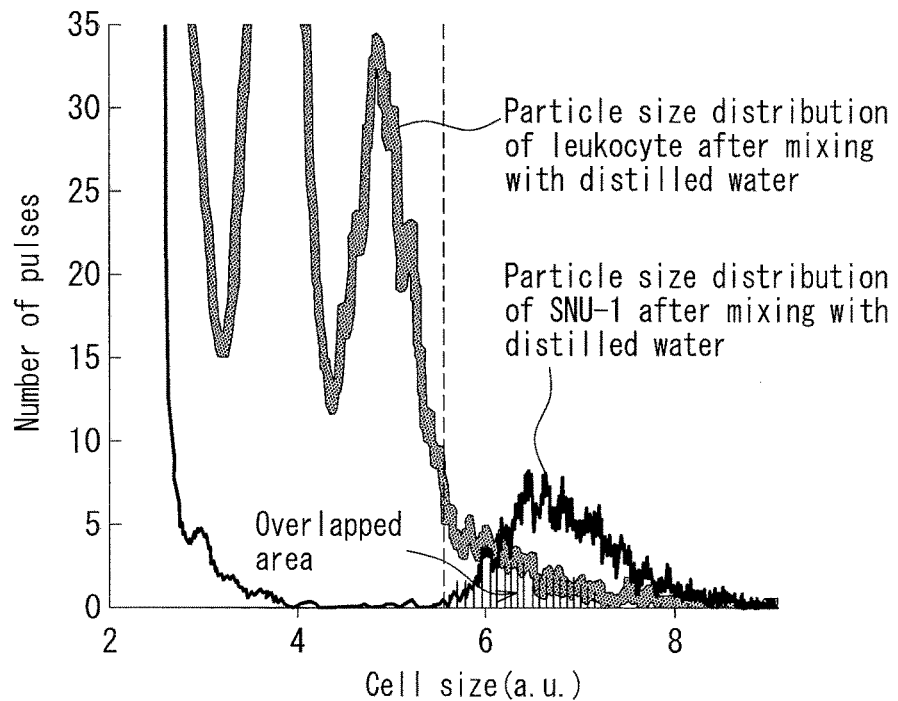

FIG. 6A and FIG. 6B show the results of a Coulter type flow cytometry analysis of a sample containing blood components, which includes a cancer cell (SNU-1) suspension or leukocytes: FIG. 6A has been treated with a surfactant mixture while FIG. 6B has not been subjected to such a treatment.

Figure 7A:
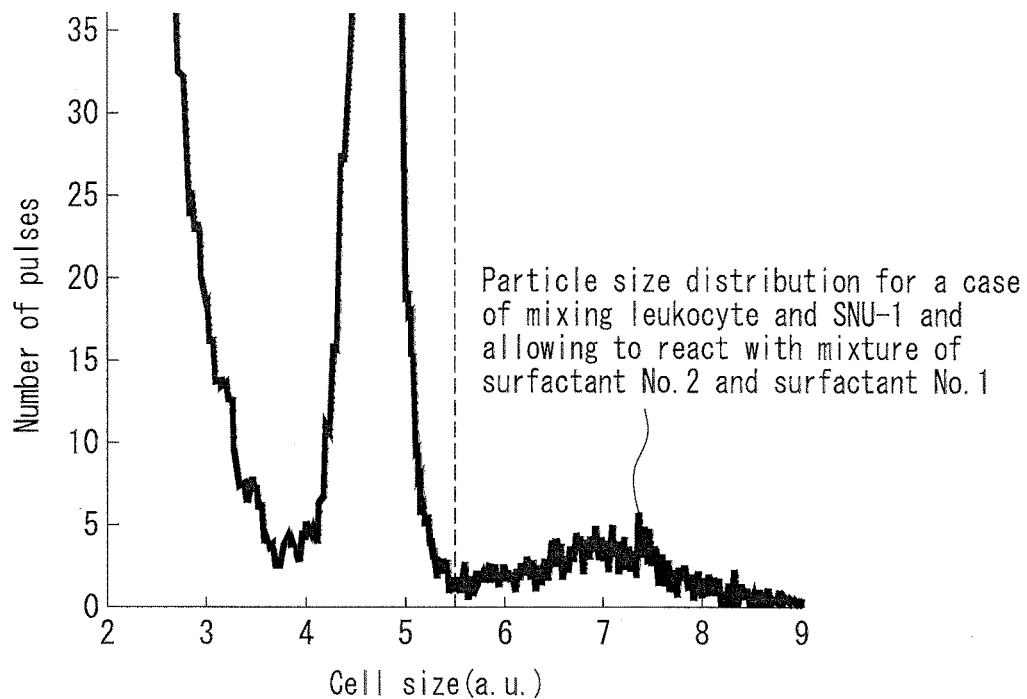
Figure 7B:
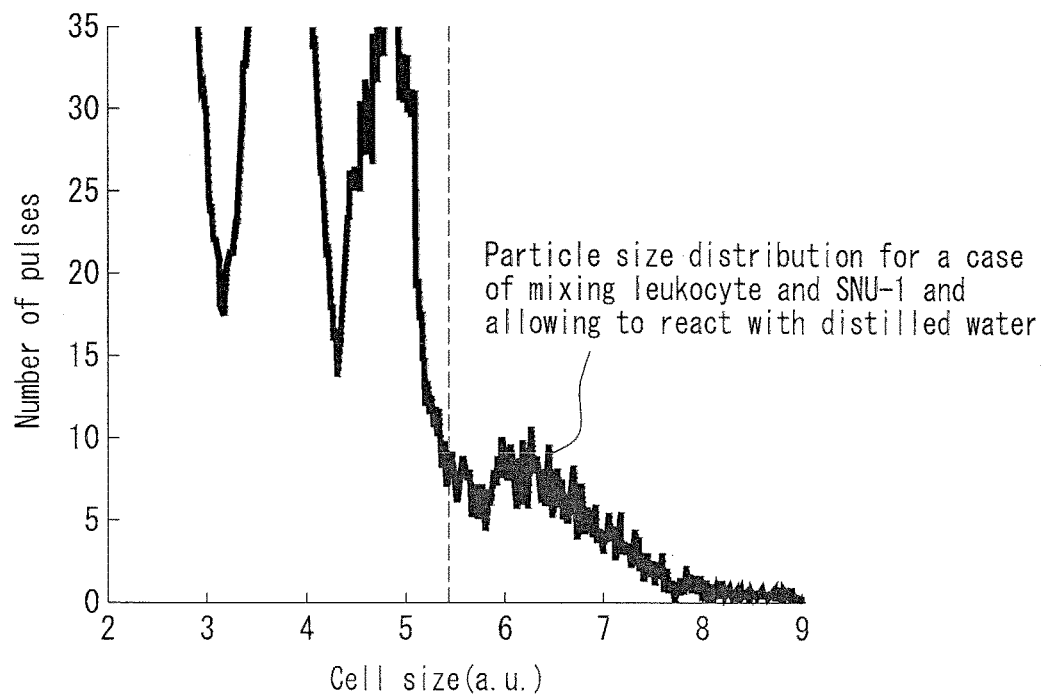

FIG. 7A and FIG. 7B show the results of a Coulter type flow cytometry analysis of a sample containing blood components, which includes cancer cells (SNU-1) and leukocytes: FIG. 7A has been treated with a surfactant mixture while FIG. 7B has not been subjected to such a treatment.

Figure 8:
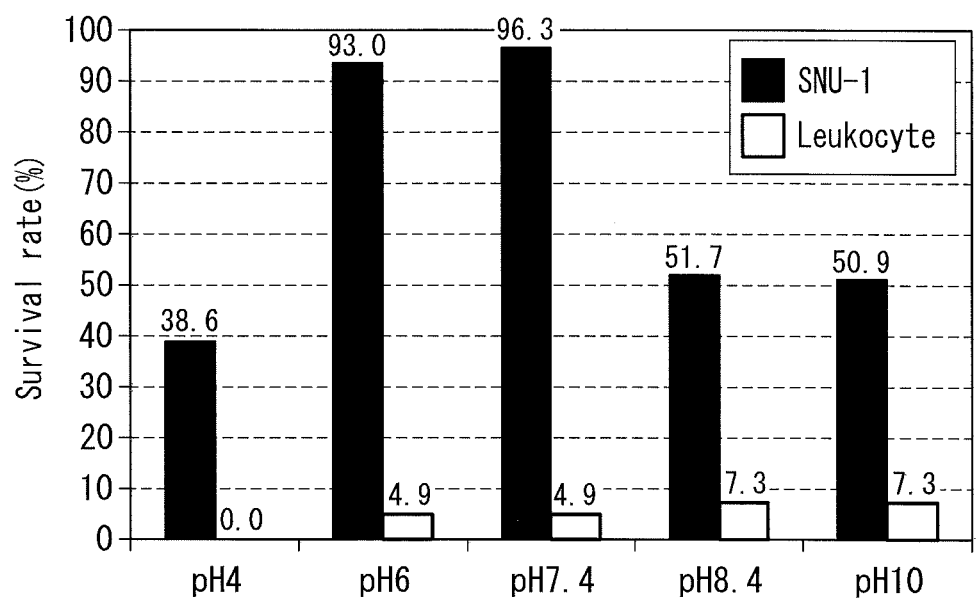

FIG. 8 is a graph showing the survival rates of samples containing blood components, which include cancer cells (SNU-1) or leukocytes suspended in a physiological saline, after a treatment with surfactant mixtures of various pHs.

DETAILED DESCRIPTION

For assaying a rare cell in a sample containing blood components or for separating and cultivating the cell, it is necessary to eliminate efficiently the cell components in the blood (in particular, erythrocytes and leukocytes) without causing serious damage to the rare cell.

Therefore, with the foregoing in mind, the disclosure provides a simple treatment method that enables removal of blood cells quickly while suppressing damage to cells other than the blood cells in the sample containing the target component. Further, the disclosure provides a simple treatment method, or separation/detection method that improves the purity of CTCs by removing blood cells and the like, thereby enabling suppression of noises at the time of counting the CTCs or measuring the nucleic acid, and also enabling detection of the CTCs.

In an embodiment, the disclosure relates to a method for treating a sample containing blood components. A sample containing blood components and a liquid containing a surfactant A are mixed with each other. In the method, no fixation agent is used, and the surfactant A is a nonionic surfactant represented by General formula (I) below.

In the formula (I), $R^1$ is a hydrocarbon group having a branched chain and having a carbon number in the range of 12 to 40, EO is an oxyethylene group, n is an average addition mole number in the range of 23 to 50, and $R^2$ is a hydrogen atom or a hydrocarbon group having a carbon number in the range of 1 to 3.

In another embodiment, the disclosure relates to a method for treating a sample containing blood components. The method includes mixing a sample containing blood components with a liquid containing a surfactant A and a surfactant B, or with a liquid containing the surfactant A and a liquid containing the surfactant B. Here, the surfactant A is a nonionic surfactant represented by General formula (I) below, and the surfactant B has a lytic property with respect to an erythrocyte higher than the corresponding lytic property of the surfactant A.

In the formula (I), $R^1$ is a hydrocarbon group having a branched chain and having a carbon number in the range of 12 to 40, EO is an oxyethylene group, n is an average addition mole number in the range of 23 to 50, and $R^2$ is a hydrogen atom or a hydrocarbon group having a carbon number in the range of 1 to 3.

In another embodiment, the disclosure relates to a method for treating a sample containing blood components. The method includes mixing a sample containing blood components with either a liquid containing a surfactant A and a surfactant B or with a liquid containing the surfactant A and a liquid containing the surfactant B. Here, the surfactant A is polyoxyetheylene octyl dodecyl ether (EO=23-50). The surfactant B is a nonionic surfactant having a lytic property with respect to an erythrocyte higher than the corresponding lytic property of the surfactant A, and it is selected from the group consisting of polyoxyethylene polyoxypropylene alkylether, polyoxyethylene octyl dodecyl ether (EO=8-22), polyoxyethylene fatty acid ester, saccharose fatty acid ester, sorbitan fatty acid ester, and a combination thereof.

In another embodiment, the disclosure relates to a method for separating or detecting a rare cell or a nucleic acid in a sample containing blood components. Here, the method includes treating a sample containing blood components by any of the treatment methods according to the disclosure, and separating or detecting a rare cell or a nucleic acid from the treated sample.

In another embodiment, the disclosure relates to a method for measuring the number of CTCs or measuring a nucleic acid of a CTC in a sample containing blood components. Here, the method includes treating a sample containing blood components by the treatment method according to the disclosure, or separating/detecting a rare cell or a nucleic acid from a sample containing blood components by the separation/detection method according to the disclosure.

In another embodiment, the disclosure relates to a method for assaying a rare cell in a sample containing blood components. Here, the method includes treating a sample containing blood components by the treatment method according to the disclosure, and subsequently assaying by a method including an observation of movements of the cell or an activity measurement.

In another embodiment, the disclosure relates to a reagent kit including the surfactant A and/or the surfactant B to be used for the treatment method according to the disclosure, the separation/detection method according to the disclosure, the method for measuring a CTC number or a CTC nucleic acid according to the disclosure, and/or the assaying method according to the disclosure.

According to the disclosure, it is possible to lyse erythrocytes and cause damage to leukocytes while suppressing damage to any cells other than the blood cells present in the sample containing the blood.

It is expected that an assay of rare cells such as a circulating tumor cells in blood will be increased further and thus there has been a demand for a simpler method that causes fewer losses. In general, tens of billions of erythrocytes and tens of millions of leukocytes are included in 10 ml of blood, while the number of CTCs in the same blood is as small as 0 to several thousands. For this reason, many technical problems exist in a direct analysis of CTCs. For example, treatments such as separation and concentration are required. Therefore, there has been a demand for a technique of concentrating and separating CTCs from blood more efficiently and/or more easily.

As a separation method utilizing an antigen-antibody reaction, there has been proposed a method of concentrating cells from blood by using magnetic beads to which an antibody has been applied and a magnetic field (see JP 3834326 and JP 2007-178193 A). However, since overcrowding blood cells that can hinder the contact of the antibody to target cells are present in the blood, it takes time for the reaction and collection of cells. Furthermore, due to the presence of the blood cells, the reaction volume is large and the amount of reagent per volume is increased, and thus the cost is raised. Furthermore, in a case of concentrating by using the beads, many blood cells are caught and thus the purity is degraded to create a false-positive. Furthermore, when a cleaning process for eliminating the blood cells is repeated, the cells of the target may be lost.

In a separation method utilizing adhesion (see WO 2005/043121 and WO 2006/078994), blood cells and blood platelets deposit on the bottom face of a typical carrier or a laboratory dish for cell cultivation. However, cancer cells cannot adhere to the laboratory dish and thus it is impossible to separate out the cancer cells. For solving this problem, proposed is a method of fixing a substance that has high affinity (such as an antibody) to the laboratory dish or to the carrier so as to allow the cells to adhere thereto. Similarly however, while there is a necessity that the cells and the substance with high affinity get contact with each other on the bottom face, the blood cells may hinder the contact. As a result, for increasing the chances of contact, it is required to devise a modification in the structure of the carrier or a method of stirring, and thus increasing the complexity of the processes.

In a centrifugation separation method, layers of the blood cells, namely a layer of erythrocytes and a layer of leukocytes in this order from the bottom, are formed after the centrifugation. Since many cancer cells have an approximate density and size to those of the leukocytes, many leukocytes are mixed with the cancer cells. Namely, the centrifugation separation is inferior in purity, resulting in a false-positive. In addition to that, the respective layers are located to be so proximate to each other that many erythrocytes are mixed in to degrade the collection rate and the purity.

Separation by a density gradient centrifugation method (JP 2010-075073 A and WO 95/20429) is used for various purposes as a method of collecting cells from the blood. However, in such a separation utilizing the density of the cells, since the size and density of the cancer cells are approximate to those of mononuclear cells of the leukocytes, many mononuclear cells are mixed in to cause the false-positive. Further in the density gradient centrifugation separation, the processes tend to be complicated. For example, it is required to collect the cells' strata without disturbing the liquid after the separation so that the respective strata will not be mixed with each other.

In a separation using a filter (WO 2006/116327 and WO 2008/155398), the difference in size of the rare cells and the deformability of the blood cells are used for separating the blood cells and the cancer cells from each other. While many erythrocytes and many leukocytes pass through the filter, a part of erythrocytes and a part of leukocytes remain on the membrane. When the pore size of the membrane is smaller than 8 µm, clogging will occur easily. In contrast, when the filtration pressure is increased to improve the efficiency in passing the blood cells through the filter, the flow rate is increased to damage the rare cells. In some cases, the rare cells may pass the pores and thus the collection rate deteriorates.

In a flow cytometry, since several millions of erythrocytes and several thousands to about ten thousands of leukocytes are present in 1 µL of blood, generally it is impossible to count the number directly. Therefore, it is required to add a hemolytic agent for eliminating the erythrocytes and to dilute the solution for detecting the respective cells at the time of measurement. It is extremely difficult to dilute the 10 mL of blood, to count the respective cells among the tens of billions of erythrocytes and hundreds of millions to several thousands of leukocytes, and to separate and count the cancer cells. In a case of an electrical resistance system, since there are leukocytes as substantially large as the cancer cells, many leukocytes are mixed in after the separation so as to cause a false-positive.

As mentioned above, the conventional separation-condensation techniques are regarded as insufficient to detect and count the rare cells with regard to a required sensitivity, efficiency and specificity, due to the survival of blood cells. If the blood cells in a sample can be treated by separation, elimination, removal or the like, in a separation using an antigen-antibody reaction, it is possible to subject the sample to centrifugation after lysis so as to allow the sample to react with a small volume of re-suspended solution, thereby shortening the reaction time and reducing the cost for the reagent. Similarly, in a separation that utilizes adhesion, cultivation and adhesion-separation become available by use of a laboratory dish for cultivation. Further in a separation that uses centrifugation-separation and density gradient centrifugation, the rare cells are collected easily. Moreover, in a case of using a filter, the analysis is carried out easily. That is, by treating the blood cells in the sample containing the blood, the error factor in counting and quantifying the rare cells (false-positive) is decreased so that quick measurement is realized.

Further, if the rare cells in the sample containing the blood can be assayed alive or can be separated and cultivated, it is possible to assay and analyze the rare cells more precisely. In general however, saponin and triton that are the nonionic surfactants utilized as hemolytic reagents for blood cell elimination, also damage rare cells such as the cancer cells so as to cause the cells to die, thereby destroying the cells. Therefore in the case of analyzing the target cell by using the surfactant, as mentioned in WO 2010/071114, the rare cells in the sample containing the blood are fixed in advance with a crosslinking reagent (a fixation reagent) such as formaldehyde and paraformaldehyde and subsequently allowed to react with the hemolytic reagent. The crosslinking agent such as formaldehyde and paraformaldehyde typically forms an intermolecular crosslink via free amino groups so as to maintain the cell membrane and the cellular structure. However, in return for the effect of maintaining the cellular structure, the fixation operation makes it difficult to conduct a separation-cultivation, observation, activity measurement, further analysis of pharmacometrics or the like for the living rare cells.

Moreover, the surfactant at the concentration recited in WO 2010/071114 cannot lyse the blood directly, and may even damage the cancer cells. Further, many leukocytes survive.

Formaldehyde and paraformaldehyde are fixation agents to be compatibly used typically in the case of using a hemolytic reagent. As the formaldehyde and the paraformaldehyde are powerful medicines, they may affect the health of the user. Although WO 2010/071114 and WO 2004/056978 describe a method of eliminating blood cells by use of ammonium chloride salt and/or a hypotonic solution, the dilution ratio is greater and thus a larger reaction tank is needed. Moreover, since the substance does not have lytic power as much as the surfactant, aggregates of cell fragments or the like will be formed easily.

The disclosure is based on the knowledge that in one or more embodiments, a surfactant A having a low lytic property with respect to erythrocytes and causing less damage to cells is used to lyse the erythrocytes while suppressing damage to rare cells present in the blood. Further, the disclosure is based on a knowledge that in one or more embodiments, a surfactant B having a powerful lytic property with respect to erythrocytes and causing more damage to rare cells and a surfactant A having low lytic property with respect to erythrocytes and causing less damage to rare cells are combined to treat the blood sample, so that it is possible to suppress damage to rare cells in the blood while lysing the erythrocytes and damaging the leukocytes. Another advantage is that these treatments can be carried out at a low cost.

Although the detail of the mechanism for enabling removal of the blood cells while suppressing damage to the rare cells in the blood by the surfactant A has not yet been clarified, the following inferences can be made. With regard to the cells, it is considered that differences in the cytoskeleton and the membrane are involved. Since the blood cells that circulate in vivo pass through the capillary vessels and the like, the cytoskeleton may deform easily. Further, the phospholipid bilayer of the cell membrane has a high flowability while the interaction between the hydrophobic parts of the phospholipid is weak. As a result, such a blood cell will be easily destroyed when it is subjected to the action of the surfactant. On the other hand, it is considered that the rare cells are rarely destroyed because specific filaments such as cytokeratin is spread across the interior of the cell and bonded to the cell membrane or the like, and the phospholipid bilayer is less flowable in comparison with the blood cells. Further, with regard to the surfactant, it is considered that the surfactant interacts with the protein, cholesterol and phospholipid on the cell membrane and lyses the cell. For the surfactant A, it is preferable that the molecular structure has a branched chain similar to the structure of a hydrophobic group of a phospholipid. The influence of the lytic power and the steric hindrance caused by the hydrophilic group is controlled by balancing the number of the added hydrophobic groups and hydrophilic groups, for example, to achieve lysing the blood cells without destroying the rare cells. However, it should be noted that the disclosure is not limited to these mechanisms.

Although the detail of the mechanism for enabling removal of blood cells while suppressing damage to the rare cells in the blood by the combination of the surfactants A and B has not been clarified yet, the following inference can be made. By combining the surfactant B having a high lytic property to the blood cells with the surfactant A, the surfactants A and B form a mixed micelle. This mixed micelle at a certain rate acts selectively on the blood cells without hindering the selectivity of the surfactant A with respect to the blood cells, and the surfactant B contacts with the blood cells and lyses blood cells rapidly with its high lytic property. Namely, it is considered that since the blood cells can be removed quickly, the damage to the cancer cells can be suppressed further. However, it should be noted that the disclosure is not limited to these mechanisms.

According to the treatment method of the disclosure, the blood cells can be removed easily while suppressing damage to the cells other than the blood cells in the sample containing the blood. Therefore, in one or more embodiments, by conducting the treatment method of the disclosure, it is possible to easily carry out the separation, condensation, measurement and/or cultivation and assay of rare cells in the blood, in particular CTCs (circulating tumor cells). Even if a leukocyte is stained in a case of staining and labeling the CTC, the leukocyte becomes a dead cell or it is damaged after the treatment according to the disclosure. Thus, the staining substance or the like leaks out and the signal (noise) from the leukocyte is lowered. Therefore, even in a nonspecific staining method that utilizes a fluorescent material accumulated within a cell or a material to be converted into a fluorescent material through metabolism (e.g., CellTracker (Green CMFDA/C7025 Invitrogen)), in one or more embodiments, a false-positive in detection, measurement, observation or the like of CTCs can be suppressed by conducting the treatment method of the disclosure.

[Sample Containing Blood Components]

In one or more embodiments, "a sample containing blood components" can be described also as "a blood-components-containing sample", which indicates a sample to which the treatment method of the disclosure can be applied, and the examples include blood, a blood-derived substance including an erythrocyte component, a bodily fluid mixed with blood or a blood-derived substance, and a sample prepared therefrom. In one or more embodiments, the "bodily fluid" may include blood, lymph, ascites, pleural fluid, cerebrospinal fluid, saliva, urine, and breast milk. An example of the blood is blood collected from a living body, and examples of the living body include the human being and animals other than the human being (e.g., mammals). Examples of the blood-derived substance containing erythrocyte components include a substance that is separated or prepared from blood and that contains an erythrocyte component or the dilution/concentrate thereof. The examples include a blood cell fraction from which blood plasma has been excluded, a blood cell concentrate, a freeze-dried substance of blood or blood cell, a sample prepared by subjecting whole blood to hemolysis, centrifuged blood, spontaneously sedimented blood, washed blood cells, specific fractions and the like. Among them, in one or plural unlimited embodiment, from the viewpoint of easy and rapid treatment and from a viewpoint of suppression of damage to rare cells in the blood, blood or a blood-derived substance(s) is used preferably for the blood containing sample.

In one or more embodiments, "a rare cell in blood" or "a rare cell in a sample containing blood components" indicates a cell other than a cellular component that can be contained in the blood of a human being or an animal other than a human being (e.g., an erythrocyte, leukocyte, and blood platelet), which includes a tumor cell and/or a cancer cell. In general, a tumor cell or a cancer cell that circulates in blood is called a CTC. The number of these rare cells in blood is in general in the range of 0 to several thousands in 10 ml of blood. In one or more embodiments, the "rare cell in blood" or the "rare cell in a sample containing blood components" indicates a cell selected from the group consisting of a cancer cell, a circular tumor cell, a vascular endothelial cell, a vascular endothelial precursor cell, a cancer stem cell, an epithelial cell, a hematopoietic stem cell, a mesenchymal cell, a fetal cell, and a combination thereof. In the present invention, in one or more embodiments, a "a nucleic acid" to be separated or detected is a nucleic acid selected from the group consisting of; RNA and DNA in a blood component; RNA and DNA in a cancer cell, a circular tumor cell, a vascular endothelial cell, a vascular endothelial precursor cell, a cancer stem cell, an epithelial cell, a hematopoietic stem cell, a mesenchymal cell and a fetal cell; and a combination thereof.

In one or more embodiments, a "removal of blood cell" indicates erythrocyte hemolysis and/or leukocyte growth inhibition. For instance, the erythrocyte hemolysis and the leukocyte growth inhibition can be checked by the method in Examples. In one or more embodiments, "leukocyte growth inhibition" may include death of a leukocyte (degradation of survival rate), hemolysis, and/or inhibition of leukocyte proliferation. In one or more embodiments, hemolysis of an erythrocyte can be observed by measuring the change in turbidity in a blood containing sample. In one or more embodiments, the degree of turbidity fluctuates a little depending on the size of the measurement cell, the standard for hemolysis may be set to reduction of the degree of turbidity to a half or less from the initial turbidity. Specifically, 30 μl of a blood containing sample and 30 μl of a reagent are mixed, which can be checked through measurement by use of a micro-plate reader. For example, in a case of a solution prepared by mixing blood with PBS or distilled water under the above-mentioned conditions, the initial turbidity is 2 to 1.5 as an absorbance value at a wavelength of 650 nm. Turbidity lowered to 0.8 or less, 0.6 or less, or 0.5 or less indicates the occurrence of hemolysis. Alternatively, in one or more embodiments, survival rate of a leukocyte in a blood containing sample which is 50% or less, less than 50%, 40% or less, less than 40%, or even 30% or less indicates occurrence of leukocyte growth inhibition.

In one or more embodiments, a liquid containing the surfactant A has the blood cell elimination effect as mentioned in the following (1).

(1) A control sample is prepared by diluting a predetermined amount of blood with distilled water so that the absorbance value measured by absorption photometry by use of a micro-plate reader and light having a wavelength of 600 nm or more will be not less than 1 and less than 2;

a test sample is prepared by replacing the distilled water for the control sample by a liquid containing 2.5 to 5 w/v % of the surfactant A;

where the absorbance value of the test sample measured by the absorption photometry by use of light having a wavelength of 600 nm or more is decreased to a half the absorbance value of the control sample within one hour.

In one or more embodiments, regarding the blood cell elimination effect of the above (1), in the liquid containing the surfactant A, the absorbance value of the test sample measured by the absorption photometry using the light having a wavelength of 600 nm or more is decreased to a half the absorbance value of the control sample within 60 minutes; within 40 minutes, or within 30 minutes.

In one or more embodiments, the liquid containing both the surfactant A and the surfactant B, or a liquid containing the surfactant A and a liquid containing the surfactant B or a mixture of the two liquids has the blood cell elimination effect as mentioned in the following (2).

(2) A control sample is prepared by diluting a predetermined amount of blood with distilled water so that the absorbance value measured by absorption photometry by use of a micro-plate reader and light having a wavelength of 600 nm or more will be 1 or more and less than 2;

a test sample is prepared by replacing the distilled water for the control sample by a liquid containing 2.5 to 5 w/v % of the surfactant A and the surfactant B;

where the absorbance value of the test sample measured by the absorption photometry by use of light having a wavelength of 600 nm or more is decreased to a half the absorbance value of the control sample within 0.5 hours.

In one or more embodiments, regarding the blood cell elimination effect of the above (2), in the liquid containing both the surfactant A and the surfactant B, a liquid containing the surfactant A and a liquid containing the surfactant B or a mixture of the two liquids, the absorbance value of the test sample measured by the absorption photometry using the light having a wavelength of 600 nm or more is decreased to half of the absorbance value of the control sample within 30 minutes; within 20 minutes, or within 15 minutes.

Regarding the test sample for assessing the blood cell elimination effect, the concentration of the surfactant A in the liquid containing the surfactant A is for example in a range of 0.001 w/v % to 10 w/v %. The total concentration of the surfactant A and the surfactant B in the liquid containing both the surfactant A and the surfactant B is for example in a range of 0.001 w/v % to 10 w/v %.

In one or more embodiments, "a combination thereof" of a group composed of number n of components may include a combination of 2 to n components in the group.

[Surfactant A]

The surfactant A to be used in the treatment method of the disclosure is a nonionic surfactant represented by General formula (I) below. The surfactant A is used alone or combined with a surfactant B having a higher lytic property with respect to an erythrocyte, thereby suppressing damage to the rare cells in the blood caused by the surfactant B while maintaining damage to the erythrocytes and the leukocytes. From the viewpoint of shortening the treatment time and further suppressing the damage to the rare cells, it is preferable that the surfactant A is combined with the surfactant B (described below) having a higher lytic property with respect to an erythrocyte.

$$R^1\text{—O-(EO)}n\text{-}R^2 \quad (I)$$

In the formula (I) above, $R^1$ is a hydrocarbon group having a branched chain and having a carbon number in the range of 12 to 40, EO is an oxyethylene group, n is an average addition mole number in the range of 23 to 50, and $R^2$ is a hydrogen atom or a hydrocarbon group having a carbon number in the range of 1 to 3.

From the viewpoint of removing the blood cells while suppressing damage to the rare cells in the blood, $R^1$ in the formula (I) is a hydrocarbon group having a branched chain and having a carbon number in the range of 12 to 40, and preferably an alkyl group having a branched chain and having a carbon number in the range of 12 to 30. In one or more embodiments, from the viewpoint of removing the blood cells while suppressing damage to the rare cells in the blood, the carbon number of the hydrocarbon group and the alkyl group is preferably in the range of 12 to 28, more preferably 14 to 26, further preferably 16 to 24, still further preferably 18 to 22, and still further preferably 20. Preferred examples for $R^1$ in the formula (I) include: an isohexyl group, an isononyl group, an isodecyl group, an isododecyl group, an isohexadecyl group, a hexyldecyl group, a hexyldodecyl group, a hexylhexadecyl group, an octyldecyl group, an octyldodecyl group, an octylhexadecyl group, a nonyldecyl group, a nonyldodecyl group, and a nonylhexadecyl group; and from the similar viewpoint, an octyldodecyl group is preferred. $R^2$ in the formula (I) is a hydrogen atom or a hydrocarbon group having a carbon number in the range of 1 to 3. In one or more embodiments, from the viewpoint of removing the blood cells while suppressing damage to the rare cells in the blood, it is a hydrogen atom or an alkyl group having a carbon number in the range of 1 to 3. In one or more embodiments, the alkyl group is a methyl group, an ethyl group, a propyl group or an isopropyl group. For the above formula (I), from the viewpoint of removing the blood cells while suppressing damage to the rare cells in the blood, a compound of formula (II) below is further preferred.

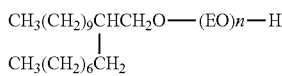

$$\begin{array}{c} CH_3(CH_2)_9CHCH_2O\!-\!\!(EO)n\!-\!H \\ | \\ CH_3(CH_2)_6CH_2 \end{array} \quad (II)$$

In one or more embodiments, from the viewpoint of removing the blood cells while suppressing damage to the rare cells in the blood, the average addition mole number n of EO in the formulae (I) and (II) is in the range of 23 to 50, preferably 24 or more, and more preferably 25 or more. From the similar viewpoint, the upper limit for n is preferably 45 or less, more preferably 40 or less, further preferably 30 or less, and still further preferably 28 or less.

In one or more embodiments, from the viewpoint of removing the blood cells while suppressing damage to the rare cells in the blood, the surfactant A is a nonionic surfactant represented by Chemical formula (1) below.

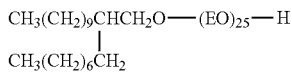

$$\begin{array}{c} CH_3(CH_2)_9CHCH_2O\!-\!\!(EO)_{25}\!-\!H \\ | \\ CH_3(CH_2)_6CH_2 \end{array} \quad (1)$$

In one or more embodiments, the surfactant A to be used in the treatment method of the disclosure is in the form of a liquid containing the surfactant A or a liquid containing the surfactants A and B. In one or more embodiments, the liquid containing the surfactant A or a liquid containing the surfactants A and B is an aqueous solution containing the surfactant A or an aqueous solution containing the surfactants A and B. For the water, distilled water, ion-exchange water, ultrapure water or the like can be used. In one or more embodiments, for the aqueous solution, a buffer and/or pH that does not lower the survival rate of the rare cells may be selected.

[Surfactant B]

The surfactant B to be used in the treatment method of the disclosure is a nonionic surfactant whose power to lyse erythrocytes is higher than that of the surfactant A. In one or more embodiments, "lysis of erythrocyte" indicates a phenomenon of hemolysis in a case of mixing the surfactant with a sample containing an erythrocyte. For example, in a case of treatment at the same concentration and/or the same mixing ratio, when the time for hemolysis is shorter, it is regarded that the power to lyse the erythrocyte is higher. Hemolysis is a phenomenon in which the cell membrane of an erythrocyte is damaged or dissolved due to various factors such as physical, chemical and biological factors, and hemoglobin or the like leaks out of the cell, resulting in the death of the erythrocyte. In one or more embodiments, from the viewpoint of removing the blood cells while suppressing damage to the rare cells in the blood, it is preferable that the surfactant B to be used in the treatment method of the disclosure has a power of inhibiting the growth of the leukocyte which is higher than that of the surfactant A.

From the viewpoint of removing the blood cells while suppressing damage to the rare cells in the blood, the surfactant B is a nonionic surfactant. In one or more embodiments, the examples include nonionic surfactants selected from the group consisting of polyoxyethylene polyoxyalkylene alkylether, polyoxyethylene alkylene ether (EO=13-22), polyoxyethylene fatty acid ester, saccharose fatty acid ester, sorbitan fatty acid ester, and a combination thereof.

In one or more embodiments, from the viewpoint of removing the blood cells while suppressing damage to the rare cells in the blood, preferably the surfactant B of polyoxyethylene polyoxyalkylene alkylether type is a nonionic surfactant represented by a formula (III) below.

$$R^3\!-\!O\text{-}(AO)m/(EO)n\text{-}R^4 \quad (III)$$

In the formula (III) above, $R^3$ is an alkyl group having a carbon number in the range of 1 to 24, $R^4$ is a hydrogen atom or an alkyl group having a carbon number in the range of 1 to 3, AO is an oxyalkylene group having a carbon number in the range of 3 to 6, EO is an oxyethylene group, m and n are average addition mole numbers of AO and EO respectively, where m is a number in the range of 1 to 100 and n is a number in the range of 0 to 50, and "/" indicates that the AO group and the EO group may be added at random or as a block regardless of the order.

In one or more embodiments, examples of $R^3$ in the formula (III) include methyl, ethyl, propyl, butyl, pentyl, hexyl, heptyl, octyl, nonyl, decyl, undecyl, dodecyl (lauryl), tridecyl, tetradecyl (myristyl), pentadecyl, hexadecyl(cetyl), heptadecyl, octadecyl (stearyl), nonadecyl, icosyl, heneicosyl, docosyl (behenyl), tricosyl, tetracosyl and the like. In the formula (III) above, $R^4$ is a hydrogen atom or a hydrocarbon group having a carbon number in the range of 1 to 3. In one or more embodiments, from the viewpoint of removing the blood cells while suppressing damage to the rare cells in the blood, it is a hydrogen atom or an alkyl group having a carbon number in the range of 1 to 3, and in one or more embodiments, the alkyl group is a methyl group, an ethyl group, a propyl group or an isopropyl group. In one or more embodiments, examples of the AO in the formula (III) include polyoxypropylene, polyoxybutylene and the like. In one or more embodiments, from the viewpoint of removing the blood cells while suppressing damage to the rare cells in the blood, m in the formula (III) is preferably in the range of 1 to 60, and more preferably 1 to 30. Similarly, n is preferably in the range of 1 to 50, and more preferably 1 to 25.

In one or more embodiments, from the viewpoint of removing the blood cells while suppressing damage to the rare cells in the blood, preferably the surfactant B of the formula (III) is a polyoxyethylene polyoxypropylene alkylether. In one or more embodiments, from the viewpoint of removing the blood cells while suppressing damage to the rare cells in the blood, the polyoxyethylene polyoxypropylene alkylether has a HLB value (hydrophilic-lipophilic balance value) in the range of 10.0 to 18.0, more preferably 12.0 to 15.0, and further preferably 12.5 to 13.5. From a similar viewpoint, preferably the polyoxyethylene polyoxypropylene alkylether has a cloudy point (° C/2% aqueous solution) in the range of 34° C. to 88° C., more preferably 40° C. to 75° C., and further preferably 50° C. to 60° C.

In one or more embodiments, examples of commercial products for the surfactant B of the formula (III) include: EMALEX DAPE-207, EMALEX DAPE-210, EMALEX DAPE-212, EMALEX DAPE-215, EMALEX DAPE-220, EMALEX DAPE-230 (all of which are manufactured by Nihon Emulsion Co., Ltd.); Plurafac (trade name) LF300, Plurafac (trade name) LF400, Plurafac (trade name) LF431, Plurafac (trade name) LF711, Plurafac (trade name) LF900, Plurafac (trade name) LF901, and Plurafac (trade name) LF1300 (all of which are manufactured by BASF Japan Ltd.); EMULGEN LS-106, EMULGEN LS-110, EMULGEN LS114, and EMULGEN MS110 (all of which are manufactured by Kao Corporation); WONDERSURF RL-80, WONDERSURF RL-100, WONDERSURF RL-140, WONDERSURF S-800, WONDERSURF S-1000, and WONDERSURF S-1400 (all of which are manufactured by AOKI OIL INDUSTRIAL CO., LTD.); and UNISAFE PKA-5015, UNISAFE PKA-5016, UNISAFE PKA-5017, and UNISAFE LM-2 (all of which are manufactured by NOF CORPORATION).

In one or more embodiments, from the viewpoint of removing the blood cells while suppressing damage to the rare cells in the blood, preferably the surfactant B of polyoxyethylene alkylether type (EO=13-22) is a nonionic surfactant represented by the formula (IV) below.

In the formula (IV) above, $R^5$ is a hydrocarbon group having a carbon number in the range of 12 to 40, EO is an oxyethylene group, n is an average addition mole number of EO in the range of 8 to 22, and $R^6$ is a hydrogen atom or a hydrocarbon group having a carbon number in the range of 1 to 3.

In one or more embodiments, from the viewpoint of removing the blood cells while suppressing damage to the rare cells in the blood, preferably $R^5$ is a hydrocarbon group having a branched chain and having a carbon number in the range of 12 to 40, more preferably an alkyl group having a branched chain and having a carbon number in the range of 12 to 30. In one or more embodiments, from the viewpoint of removing the blood cells while suppressing damage to the rare cells in the blood, preferably the carbon number of the hydrocarbon group and the alkyl group is in the range of 12 to 28, more preferably 14 to 26, further preferably 16 to 24, still further preferably 18 to 22, and still further preferably 20. Preferred examples for $R^5$ of the formula (IV) include an isohexyl group, an isononyl group, an isodecyl group, an isododecyl group, an isohexadecyl group, a hexyldecyl group, a hexyldodecyl group, a hexylhexadecyl group, an octyldecyl group, an octyldodecyl group, an octylhexadecyl group, a nonyldecyl group, a nonyldodecyl group, and a nonylhexadecyl group; and from the similar viewpoint, an octyldodecyl group is preferred. $R^6$ in the formula (IV) is a hydrogen atom or a hydrocarbon group having a carbon number in the range of 1 to 3. In one or more embodiments, from the viewpoint of removing the blood cells while suppressing damage to the rare cells in the blood, it is a hydrogen atom or an alkyl group having a carbon number in the range of 1 to 3, and in one or more embodiments, the alkyl group is a methyl group, an ethyl group, a propyl group or an isopropyl group. For the formula (IV), from the viewpoint of removing the blood cells while suppressing damage to the rare cells in the blood, a formula (V) below is further preferred.

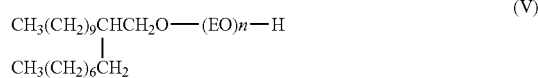

In one or more embodiments, from the viewpoint of removing the blood cells while suppressing damage to the rare cells in the blood, preferably the average addition mole number n of the EO in the formulae (IV) and (V) is in the range of 10 to 22, more preferably 13 to 22, further preferably 15 to 21, still further preferably 18 to 21, and still further preferably 20.

In one or more embodiments, the surfactant B of polyoxyethylene fatty acid ester type is a nonionic surfactant represented by a formula (VI) below.

In the formula (VI) above, $R^7$ is a hydrocarbon group having a carbon number in the range of 10 to 40, EO is an oxyethylene group, n is an average addition mole number of EO in the range of 6 to 160, and $R^8$ is a hydrogen atom or a hydrocarbon group having a carbon number in the range of 1 to 3.

From the viewpoint of removing the blood cells while suppressing damage to the rare cells in the blood, $R^7$ in the above formula (VI) is a hydrocarbon group having a carbon number in the range of 10 to 40. In one or more embodiments, it is an alkyl group having a carbon number in the range of 10 to 30. In one or more embodiments, from the viewpoint of removing the blood cells while suppressing damage to the rare cells in the blood, the carbon number of the hydrocarbon group and the alkyl group is in the range of 10 to 20, 10 to 18, 10 to 16, or 12. $R^8$ in the above formula (VI) is a hydrogen atom or a hydrocarbon group having a carbon number of 1 to 3. In one or more embodiments, from the viewpoint of removing the blood cells while suppressing damage to the rare cells in the blood, it is a hydrogen atom or an alkyl group having a carbon number in the range of 1 to 3. In one or more embodiments, the alkyl group is a methyl group, an ethyl group, a propyl group or an isopropyl group. In one or more embodiments, from the viewpoint of removing the blood cells while suppressing damage to the rare cells in the blood, the average addition mole number n of EO in the formula (VI) is in the range of 6 to 20, 8 to 18, 10 to 16, or 12. In one or more embodiments, from the viewpoint of removing the blood cells while suppressing damage to the rare cells in the blood, the surfactant B in the formula (VI) is polyoxyethylene (12) monolaurate.

In one or more embodiments, the surfactant B is a nonionic surfactant having a sugar moiety as a hydrophilic part and either a fatty acid chain or an alkyl chain as a hydrophobic part.

There is no particular limitation on the sugar moiety and the examples include sugar moieties of monosaccharide, disaccharide, oligosaccharide and the like. The number of the monosaccharides in the sugar moiety is not limited in particular, and it may be in the range of 1 to 20 for example. Although there is no particular limitation on the sugar moiety of the monosaccharide, the examples include glucose residue, galactose residue, mannose residue, thioglucose residue, arabinose residue, xylose residue, glucuronic acid residue, and glucosamine residue. Although there is no particular limitation on the sugar moiety of the disaccharide, the examples include sucrose residue (saccharose residue), lactose residue, maltose residue, and thiomaltose residue; preferably, sucrose residue.

There is no particular limitation on the fatty acid chain, and the examples include fatty acid residue and an alkyl group. There is no particular limitation on the fatty acid residue, and it may be a saturated fatty acid residue or an unsaturated fatty acid residue for example. Examples of the fatty acid residue include, without any particular limitations, a linear fatty acid residue, a branched fatty acid residue, and a cyclic fatty acid residue. The carbon number of the fatty acid residue is not limited particularly, and it is in the range of 4 to 28 for example, and preferably in the range of 10 to 22. Although there is no particular limitation on the saturated fatty acid residue, the examples include a capric acid residue, a lauric acid residue, a myristic acid residue, a pentadecylic acid residue, a palmitic acid residue, a stearic acid residue, an arachidic acid residue, and a behenic acid residue. Preferably, they are acyl groups such as a decanoyl group, a dodecanoyl group, a tetradecanoyl group, a pentadecanoyl group, a hexadecanoyl group, an octadecanoyl group, an icosanoyl group and a docosanoyl group. Although there is no particular limitation on the unsaturated fatty acid residue, the examples include an oleic acid residue, and a linoleic acid residue. For example, acyl groups such as a cis-9-octadecenoyl group and a cis,cis-9,12-octadeoctadecadinoyl group are preferred. For the fatty acid residue, from the viewpoint of removing the blood cells while suppressing damage to the rare cells in the blood, the capric acid residue and the lauric acid residue are preferred.

The alkyl group is not limited particularly. For example, it may be a linear alkyl group or a branched alkyl group. The carbon number of the alkyl group is not limited particularly, and for example, it may be in the range of 1 to 18. Specific examples of the alkyl groups include, without any particular limitation, a methyl group, an ethyl group, a n-propyl group, an isopropyl group, a n-butyl group, an isobutyl group, a sec-butyl group, a tert-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, an nonadecyl group, and an icosyl group.

Specific examples of the nonionic surfactant having a sugar moiety include, without any particular limitation, saccharose (sucrose) fatty acid ester, alkylglucoside, and alkyl oligosaccharide.

Although there is no particular limitation on the saccharose (sucrose) fatty acid ester, the examples include sucrose caprate, sucrose laurate, sucrose myristate, sucrose palmitate, sucrose stearate, sucrose behenate, sucrose oleate, and sucrose linoleate; preferably, sucrose caprate and sucrose laurate. There is no particular limitation on the saccharose (sucrose) fatty acid ester, and the examples include monoester, diester, and triester. Although there is no particular limitation on the saccharose fatty acid monoester, the examples include sucrose monocaprate, sucrose monolaurate, sucrose monomyristate, sucrose monopalmitate, sucrose monostearate, sucrose monobehenate, sucrose monooleate, and sucrose monolinoleate; preferably, sucrose monocaprate and sucrose monolaurate. Although there is no particular limitation on the saccharose fatty acid diester, the examples include sucrose dicaprate, sucrose dilaurate, sucrose dimyristate, sucrose dipalmitate, sucrose distearate, sucrose dibehenate, sucrose dioleate, and sucrose dilinoleate; preferably, sucrose dicaprate and sucrose diaurate. Although there is no particular limitation on the saccharose fatty acid triester, the examples include sucrose tricaprate, sucrose trilaurate, sucrose trimyristate, sucrose tripalmitate, sucrose tristearate, sucrose tribehenate, sucrose trioleate, and sucrose trilinoleate; preferably, sucrose tricaprate and sucrose triaurate.

The saccharose fatty acid ester may be any of the monoester, the diester, the triester and the like, or it may be a mixture thereof. Preferably the saccharose fatty acid ester contains the monoester for example. Although there is no particular limitation on the content of the saccharose fatty acid monoester, it is in the range of 50 to 100% by weight for example, and preferably in the range of 70 to 100% by weight.

Although there is no particular limitation on the alkylglucoside, the examples include n-octyl-β-D-glucoside, n-dodecyl-β-maltoside, n-decyl-β-maltoside, n-octyl-β-D-maltoside, 3-oxatridecyl-α-D-mannoside, n-heptyl-β-thioglucoside, n-nonyl-β-D-thiomaltoside, and n-octyl-β-D-thioglucoside.

In one or more embodiments, the surfactant B to be used in the treatment method of the disclosure is provided in a form of a liquid containing the surfactant B or a liquid containing the surfactants A and B. In one or more embodiments, the liquid containing the surfactant B or the liquid containing the surfactants A and B is an aqueous solution containing the surfactant B or an aqueous solution containing the surfactants A and B. For the water, distilled water, ion-exchange water, ultrapure water or the like can be used. In one or more embodiments, for the aqueous solution, a buffer and/or pH that does not lower the survival rate of the rare cells may be selected.

The nonionic surfactants A and B may be used alone or in combination of two or more.

[Method for Treating a Sample Containing Blood Components]

In one or more embodiments, the disclosure relates to a method for treating a sample containing blood components. According to the method, a sample containing blood components is mixed with a surfactant A or with the surfactants A and B. In one or more embodiments, the method for treating a sample containing blood components according to the disclosure is a method of lysing erythrocytes while suppressing degradation in the survival rate of the rare cells that may be contained in the sample, and/or degrading the survival rate of leukocytes. Therefore, in the method for treating a sample containing blood components according to the disclosure, it is preferable that the rare cells are not fixed or any fixation agent that can lower the survival of the rare cells is not used. In the disclosure, "fixation" includes immobilizing the structures of cells and cell organelle while keeping the living form. Therefore, in one or more embodiments, "not fixing" includes maintaining a state capable of morphological transformation and/or suppressing any factors that may inhibit the morphological transformation.

The fixation agent includes a crosslinking reagent. The crosslinking reagent denotes a reagent capable of maintaining a cell membrane and a cellular structure by forming an intermolecular crosslink via free amino groups. Specific examples of the fixation agent include formaldehyde, paraformaldehyde, trioxane, and glutaraldehyde. Other than the crosslinking reagent, organic solvents such as acetone and alcohols such as methanol and ethanol may be included.

In one or more embodiments, the method of treating a sample containing blood components according to the disclosure includes mixing a sample containing blood components with a liquid containing a surfactant A, or with either a liquid containing surfactants A and B or a liquid containing the surfactant A and a liquid containing the surfactant B. In one or more embodiments, the method includes adding to the sample containing blood components an aqueous solution containing the surfactant A or an aqueous solution containing surfactants A and B or an aqueous solution containing the surfactant A and an aqueous solution containing the surfactant B, and mixing. In one or more embodiments, addition of the liquid containing the surfactant A and the liquid containing the surfactant B may be an embodiment of adding any one of the surfactants first and then adding the other; or it may be an embodiment of adding both the surfactants at the same time. Among them, in one or more embodiments of a method of mixing a sample containing blood components with the surfactants A and B, from the viewpoint of removing the blood cells while suppressing damage to the rare cells in the blood, it is preferable that the sample containing blood components and the surfactants A and B are mixed quickly to form a homogeneous mixture.

In one or more embodiments, from the viewpoint of removing the blood cells while suppressing damage to the rare cells in the blood, and from the viewpoint of carrying out the treatment more easily and quickly, it is preferable that the temperature for the treatment method of the disclosure is in the range of 0 to 50° C., more preferably 4 to 40° C., and further preferably 10 to 37° C. Preferably the temperature indicates a temperature at the time of allowing the sample containing the blood component to react with the surfactant A or with the surfactants A and B.

In one or more embodiments, in the treatment method of the disclosure, it is preferable that after mixing the sample containing the blood component with either the surfactant A or the surfactants A and B, for removing the blood cells, the mixture is allowed to stand or stirred for a period of time. In one or more embodiments, from the viewpoint of removing the blood cells while suppressing damage to the rare cells in the blood, and from the viewpoint of carrying out the treatment more easily and quickly, preferably the predetermined period of time is 0 to 60 minutes, more preferably 1 to 30 minutes, and further preferably 1 to 15 minutes.

It is preferable that the concentration of the surfactant B aqueous solution to be mixed with the sample containing the blood component is an amount to lyse erythrocytes such that in a case of mixing the surfactant B aqueous solution alone with the sample containing the blood component, under a condition of 10 to 0.01 w/v % and at an ambient temperature of 25° C., in a measurement with a typical micro-plate reader, in a case of allowing 30 μL, of the solution to react with equal parts of the sample containing the blood component, the absorbance becomes 0.8 or less, more preferably 0.6 or less and further preferably 0.5 or less at the wavelength of 650 nm.

In one or more embodiments, it is preferable that the concentration of the surfactant B aqueous solution before being mixed with the sample containing blood components is in the range of 0.01 to 10 w/v %, more preferably 0.01 to 5 w/v %, and further preferably 0.01 to 2.5 w/v % in a case where the sample is blood, from the viewpoint of removing the blood cells while suppressing damage to the rare cells in the blood, and from the viewpoint of carrying out the treatment more easily and quickly. In one or more embodiments, it is preferable that the final concentration of the surfactant B in a case of mixing the sample with the surfactants A and B is in the range of 0.01 to 5 w/v %, more preferably 0.01 to 1.25 w/v %, and further preferably 0.01 to 0.5 w/v % in a case where the sample is blood, from the viewpoint of removing the blood cells while suppressing damage to the rare cells in the blood, and from the viewpoint of carrying out the treatment more easily and quickly. The concentrations can be adjusted suitably in a case where the sample is prepared by concentrating or diluting blood. In the disclosure, w/v % is a unit expressing the weight (gram) of a solute dissolved in 100 ml of the solution. For example, in a case where 5 g of a solute is dissolved in 100 ml of a solution, it is recited as 5 w/v %.

In one or more embodiments, it is preferable that the concentration of the surfactant A aqueous solution before being mixed with the blood sample is in the range of 0.01 to 10 w/v %, more preferably 0.05 to 5 w/v %, and further preferably 0.5 to 5 w/v % in a case where the blood sample is blood, from the viewpoint of removing the blood cells while suppressing damage to the rare cells in the blood, and from the viewpoint of carrying out the treatment more easily and quickly. In one or more embodiments, it is preferable that the final concentration of the surfactant A in a case of mixing the blood sample with either the surfactant A or with the surfactants A and B is in the range of 0.01 to 10 w/v %, more preferably 0.05 to 5 w/v %, and further preferably 0.5 to 5 w/v % in a case where the blood sample is blood, from the viewpoint of removing the blood cells while suppressing damage to the rare cells in the blood, and from the viewpoint of carrying out the treatment more easily and quickly. The concentrations can be adjusted suitably with reference to the above-mentioned concentration in a case where the sample is prepared by concentrating or diluting blood.

The quantity ratio of the surfactant A to the surfactant B both of which are to be mixed with the sample containing blood components can be adjusted suitably from the viewpoint of removing the blood cells while suppressing damage to the rare cells in the blood. In one or more embodiments, the quantity ratio of the surfactant A to the surfactant B (A/B) in the mixture is 50/50 or more for example. From the viewpoint of suppressing damage to the rare cells in the blood, preferably it is 60/40 or more, more preferably 70/30 or more, and further preferably 80/20 or more. Further in one or more embodiments, from the viewpoint of removing the blood cells quickly, it is preferable that the quantity ratio of the surfactant A to the surfactant B (A/B) in the mixture (weight ratio) is less than 100/0, and more preferably less than 99/1. In conclusion, in one or more embodiments, from the viewpoint of removing the blood cells while suppressing damage to the rare cells in the blood, the quantity ratio of the surfactant A to the surfactant B (A/B) in the mixture (weight ratio) is for example not less than 50/50 and less than 100/0, preferably in the range of 60/40 to 99/1, more preferably 70/30 to 99/1, and further preferably 80/20 to 95/5. Here, "less than 100/0" indicates that the surfactant B of more than 0% is contained.

In one or more embodiments, from the viewpoint of suppressing damage to the rare cells in the blood, the total concentration of the surfactant A and the surfactant B at the time of being mixed with a sample containing blood components is preferably 10 w/v % or less, more preferably 5 w/v % or less, further preferably 2.5 w/v % or less, still further preferably 1.25 w/v % or less, and still further preferably 0.75 w/v % or less. Although there is no particular lower limit of the concentration, a concentration to remove blood cells can be set appropriately, which is for example 0.002 w/v % or more, 0.02 w/v % or more, or 0.04 w/v % or more, in one or more embodiments.

Depending on the form of the sample containing blood components, a buffer and an osmotic regulator can be added to the surfactant solution (which is an aqueous solution selected from the group consisting of an aqueous solution containing the surfactant A, an aqueous solution containing the surfactants A and B, and a solution containing the surfactant B; the same shall apply hereinafter). For example, in a case of separating rare cells from blood and subsequently allowing the rare cells to react with the surfactant solution for the purpose of eliminating any mixed blood cells, any known buffer and/or osmotic regulator can be added to the surfactant solution as long as the cancer cells are not damaged. In one or more embodiments, in the case where rare cells in blood are suspended in a solution including no serum such as a physiological solution or a buffer solution, from the viewpoint of suppressing damage to the rare cells present in the blood, the pH of a reaction solution after mixing therein the surfactant solution is preferably 5.0 to 9.0, 5.5 to 8.4, 6.0 to 8.4, 5.5 to 8.0, 6.0 to 8.0, 6.0 to 7.7, 6.0 to 7.5 or 6.0 to 7.4. In one or more embodiments, the surfactant solution may have pH of 6 to 9 and the osmotic pressure of 0 to 400 mOsm. In the case of a direct reaction with a sample containing blood components, in one or more embodiments, the surfactant solution containing the surfactant alone may be mixed. Alternatively, the pH may be adjusted in the above-mentioned range. The buffer is not limited particularly, and the examples include a phosphoric acid physiological buffer solution (PBS), a citric acid buffer solution, a HEPES buffer solution, an ADA (N-(2-acetamide) iminodiacetic acid) buffer solution, a MES (2-morpholino ethane sulfonic acid) buffer solution, a bis-tris(bis-(2-hydroxyethyl) imino-tris-(hydroxymethyl methane) buffer solution, a PIPES (piperazine-1,4-bis(2-ethane sulfonic acid)) buffer solution, an ACES (N-(2-acetamido)-2-aminoethane sulfonic acid) buffer solution, a MOPSO (2-hydroxy-3-morpholino propane sulfonic acid) buffer solution, a BES (N,N-bis(2-hydrozyethyl)-2-aminoethane sulfonic acid) buffer solution, and HEPES (2-[4-(2-hydroxyethyl)-1-piperazinyl]ethane sulfonic acid) buffer solution. Examples of the osmotic regulator include ethylene glycol and sodium chloride. A nucleic acid, which has been obtained from broken leukocytes may be measured, decomposed, and/or eliminated by using any known technique.

[Method for Separating or Detecting a Rare Cell or a Nucleic Acid in Blood]

In the sample containing blood components after the treatment of the disclosure, the erythrocytes are lysed and growth of the leukocytes is inhibited while damage to the rare cells (if such cells exist) in the blood is suppressed. The rare cells or the nucleic acids may be separated or detected from the sample in this state. Therefore, the disclosure in its aspect relates to a method for separating or detecting rare cells in blood, and the method includes treating a sample containing blood components by the treatment method of the disclosure, and separating or detecting the rare cells or the nucleic acids from the treated sample containing the blood components.

In one or more embodiments, separation or detection of the rare cells can be carried out by using a method for example separation by use of affinity, density separation, centrifugation separation, adhesion separation, sizing separation, flow cytometry, electrical separation, magnetic separation, sowing on a medium, and a combination thereof. Before the separation, if necessary, the sample containing the blood component that has been treated according to the method of the disclosure may be diluted to lower the viscosity and/or the density of the solution. In one or more embodiments, the separation/detection method of the disclosure may include isolating the rare cells and/or concentrating the rare cells.

Further, in one or more embodiments, the disclosure relates to a method for separating or detecting rare cells or nucleic acids in a sample containing blood components, and the method includes separation of rare cells or fractions including a nucleic acid from a sample containing blood components, and, treating the separated fractions by the method of the disclosure, thereby separating or detecting the rare cells or the nucleic acids from the treated fractions.

In one or more embodiments, in an example of the separation method using affinity, the rare cells are separated by using a solid phase (e.g., beads or a plate) where an antibody with respect to the surface antigen of the rare cells or a probe has been immobilized. In one or more embodiments, in an example of the separation method using adhesion, the rare cells are separated by using a solid phase (e.g., beads or a plate) where molecules to adhere to the surface adhesive molecules of the rare cells have been immobilized. In one or more embodiments, an example of the separation method utilizing density includes a separation dependant on density of the rare cells by any of various density gradient centrifugations. In one or more embodiments, an example of the centrifugation separation includes a separation by centrifugation-precipitation of the rare cells. In one or more embodiments, the sizing separation includes separation of rare cells by filtration using a filter having an appropriate pore size. In one or more embodiments, the flow cytometry includes fluorescent labeling and/or immunostaining surface markers of rare cells and separating with reference to the signal. Furthermore, in one or more embodiments, it is possible to cultivate on a medium a sample containing blood components after being subjected to the treatment of the disclosure and to select any growing cells. The rare cells separated in this manner can be used for an assay or a further cultivation. Alternatively in one or more embodiments, the thus separated rare cells can be separated further on the basis of the electrical or magnetic characteristics. By using any detection method suitable for these separation methods, the rare cells or the nucleic acids in the sample containing blood components can be detected. In one or more embodiments, examples of the detection method include a detection method utilizing a radioactive substance, a detection method utilizing a luminous phenomenon, a detection method utilizing a pigment, a detection method utilizing magnetism, an electric detection method, an optical detection method, and detection method including labeling by use of the labeling method associated with a detection method selected from the group consisting of these methods and a combination thereof.

In one or more embodiments of the disclosure, it is also possible to carry out the treatment of the disclosure and/or the separation or detection of the disclosure with respect to the sample containing the blood components that has been subjected to the treatment of the disclosure and/or the fractions containing the rare cells separated by the treatment of the conventional technique or fractions from which the rare cells have been removed. As a result of these treatments, it is possible to improve the collection rate of the rare cells, or to improve the purity of the rare cells.

[Labeling Treatment with Respect to Rare Cells in Blood]

In the treatment method of the disclosure, labeling with respect to the rare cells in blood may be carried out concurrently. Labeling of rare cells is effective in the above-mentioned separation/detection method of the disclosure and also in the CTC number measurement method mentioned below, and furthermore it may be effective in assay of rare cells after separation. Therefore, in one or more embodiments, the treatment method of the disclosure includes a labeling treatment. Further, labeling of rare cells is effective in the below-mentioned CTC number measurement method, and also may be effective in assay of rare cells after separation. Therefore, in one or more embodiments, the separation/detection method of the disclosure includes a labeling treatment.

The labeling treatment can be carried out for example by allowing a known labeling reagent to contact with the rare cells. Typically, it can be carried out by mixing the labeling reagent with a sample containing blood components. The timing for mixing the labeling reagent in the sample containing the blood components may be before, simultaneously or after addition of the surfactants A and B or may be after separation of the rare cells. Among them, from the viewpoint of reducing the cost for the reagent, preferably the labeling treatment is carried out after separation and concentration. Although there is no particular limitation on the labeling, in one or more embodiments, the examples include radioactive labeling, fluorescent pigment labeling, pigment staining or labeling, magnetic labeling, charge labeling, and a combination thereof, each of which can be carried out by use of a suitable labeling reagent.

[Method for Assaying Rare Cells in a Sample Containing Blood Components]

In any other aspect, the disclosure can relate to a method for assaying rare cells in a sample containing blood components, where the method includes treating a sample containing blood components by a method of the disclosure and then assaying by a method including observation of movement of the cells or activity measurement.

[CTC Number Measurement Method]

It has been reported that the number of CTCs in blood correlates with possibility of metastasis or prognosis of cancer. And thus, it has been known to measure the CTC number in blood for providing a guideline of diagnosis, prognosis, prediction/judgment of treatment effect of cancer. According to the treatment method of the disclosure and/or the separation/detection method of the disclosure, a separation can be carried out while suppressing damage to the CTC as a rare cell. Alternatively, the nucleic acid of a CTC may be measured. Therefore, in another aspect, the disclosure includes treating a sample containing blood components by the treatment method of the disclosure, and/or, separating a CTC from the sample containing the blood components by the separation/detection method of the disclosure. Counting of the CTC number or measurement of the nucleic acid of a CTC may be carried out at the same time of separation by the flow cytometry after an appropriate labeling treatment for example, or the separated cells may be counted by observation under a microscope. Alternatively, the measurement may be carried out based on fluorimetry from the viewpoint of morphology of cancer cells or the quantities of DNA and/or RNA.

[Reagent Kit]

In a still another aspect, the disclosure relates to a reagent kit to be used for the treatment method of the disclosure, the separation/detection method of the disclosure, and/or the CTC number measurement method of the disclosure. The reagent kit contains the surfactant A or the surfactants A and B. In one or more embodiments, the reagent kit of the disclosure may contain further a labeling reagent for labeling the rare cells or CTC. For the labeling reagent, any of the above-mentioned reagents can be used. In another aspect, the reagent kit of the disclosure may include an instruction manual reciting the treatment method of the disclosure, the separation/detection method of the disclosure, and/or, the CTC number measurement method of the disclosure. For the reagent kit of the disclosure, the instruction manual may not be packed with the reagent kit of the disclosure but be supplied on web.

Namely, the disclosure can further relate to the one or more embodiments below.

[A1] A method for treating a sample containing blood components, the method comprising mixing a sample containing blood components with a surfactant A, or mixing the sample with a liquid containing the surfactant A, wherein from the viewpoint of suppressing damage to a rare cell, it is preferable that no fixation agent is used selectively, and wherein the surfactant A is a nonionic surfactant represented by General formula (I) below:

$$R^1\text{—O-(EO)}n\text{-}R^2 \tag{I}$$

In the formula (I), $R^1$ is a hydrocarbon group having a branched chain and having a carbon number in the range of 12 to 40, EO is an oxyethylene group, n is an average addition mole number of EO in the range of 23 to 50, and $R^2$ is a hydrogen atom or a hydrocarbon group having a carbon number in the range of 1 to 3.

[A2] A method for treating a sample containing blood components, the method comprising mixing a sample containing blood components with a surfactant A and a surfactant B, or mixing the sample with a liquid containing both the surfactant A and the surfactant B or with a liquid containing the surfactant A and a liquid containing the surfactant B, wherein from the viewpoint of suppressing damage to a rare cell, it is preferable that no fixation agent is used selectively, wherein the surfactant A is a nonionic surfactant represented by General formula (I) below, and wherein the surfactant B has a lytic property with respect to an erythrocyte higher than the corresponding lytic property of the surfactant A.

$$R^1\text{—O-(EO)}n\text{-}R^2 \tag{I}$$

In the formula (I), $R^1$ is a hydrocarbon group having a branched chain and having a carbon number in the range of 12 to 40, EO is an oxyethylene group, n is an average addition mole number of EO in the range of 23 to 50, and $R^2$ is a hydrogen atom or a hydrocarbon group having a carbon number in the range of 1 to 3.

[A3] The method for treating a sample containing blood components according to [A1] or [A2], wherein the surfactant A is polyoxyethylene alkylene ether (EO=23-35).

[A4] The method for treating a sample containing blood components according to [A1] or [A3], wherein the surfactant B is a nonionic surfactant selected from the group consisting of polyoxyethylene polyoxyalkylene alkylether, polyoxyethylene alkylene ether, (EO=13-22), polyoxyethylene fatty acid ester, saccharose fatty acid ester, sorbitan fatty acid ester, and a combination thereof.

[A5] The method for treating a sample containing blood components according to any one of [A2] and [A4], wherein the surfactant B is a nonionic surfactant represented by General formula (III) below.

$$R^3\text{—O-(AO)}m/\text{(EO)}n\text{-}R^4 \tag{III}$$

In the formula (III), $R^3$ is an alkyl group having a carbon number in the range of 1 to 24, $R^4$ is a hydrogen atom or an alkyl group having a carbon number in the range of 1 to 3, AO is an oxyalkylene group having a carbon number in the range of 3 to 6, EO is an oxyethylene group, m and n are average addition mole numbers of AO and EO respectively, specifically, m is a number in the range of 1 to 100 and n is a number in the range of 0 to 50, and "I" indicates that the AO group and the EO group may be added at random or as a block regardless of the order.

[A6] The method for treating a sample containing blood components according to any one of [A2] to [A5], wherein the surfactant B is a nonionic surfactant represented by General formula (IV) below.

$$R^5\text{—O-(EO)}n\text{-}R^6 \tag{IV}$$

In the formula (IV), $R^5$ is a hydrocarbon group having a carbon number in the range of 12 to 40, EO is an oxyethylene group, n is an average addition mole number of EO in the range of 8 to 22, and $R^6$ is a hydrogen atom or a hydrocarbon group having a carbon number in the range of 1 to 3.

[A7] The method for treating a sample containing blood components according to any one of [A2] to [A6], wherein the surfactant B is a nonionic surfactant represented by General formula (VI) below.

$$R^7\text{—COO-(EO)}n\text{-}R^8 \tag{VI}$$

In the formula (VI), $R^7$ is a hydrocarbon group having a carbon number in the range of 10 to 40, EO is an oxyethylene group, n is an average addition mole number of EO in the range of 6 to 160, and $R^8$ is a hydrogen atom or a hydrocarbon group having a carbon number in the range of 1 to 3.

[A8] The method for treating a sample containing blood components according to any one of [A2] to [A7], wherein the surfactant B is a surfactant having a sugar moiety as a hydrophilic part and either a fatty acid chain or an alkyl chain as a hydrophobic part.

[A9] The method for treating a sample containing blood components according to any one of [A2] to [A8], wherein the surfactant B is saccharose laurate.

[A10] A method for treating a sample containing blood components, the method comprising mixing a sample containing blood components with a surfactant A and a surfactant B, or mixing the sample with a liquid containing both the surfactant A and the surfactant B or with a liquid containing the surfactant A and a liquid containing the surfactant B, wherein from the viewpoint of suppressing damage to a rare cell, it is preferable that no fixation agent is used selectively, wherein the surfactant A is polyoxyethylene octyl dodecyl ether (EO=23-50); the surfactant B is a nonionic surfactant having a lytic property with respect to an erythrocyte higher than the corresponding lytic property of the surfactant A, and selected from the group consisting of polyoxyethylene polyoxypropylene alkylether, polyoxyethylene octyldodecy ether, (EO=8-22), polyoxyethylene fatty acid ester, saccharose fatty acid ester, sorbitan fatty acid ester, and a combination thereof.

[A11] The method for treating a sample containing blood components according to any one of [A2] to [A10], wherein the quantity ratio of the surfactant A to the surfactant B (A/B) in the mixture (weight ratio) is not less than 50/50 and less than 100/0.

[A12] The method for treating a sample containing blood components according to any one of [A1] to [A11], wherein the liquid containing the surfactant A has a blood cell elimination effect as described in the following (1):
(1) preparing a control sample by diluting a predetermined amount of blood with distilled water so that an absorbance value measured by an absorption photometry by use of a micro-plate reader and light of a wavelength of not less than 600 nm is not less than 1 and less than 2; preparing a test sample by use of a liquid containing the surfactant A in place of the distilled water in the control sample, so that the time for the absorbance value of the test sample measured by an absorption photometry by use of light having a wavelength of not less than 600 nm is decreased to a half the absorbance value of the control sample is not more than one hour.

[A13] The method for treating a sample containing blood components according to any one of [A1] to [A12], wherein the liquid containing the surfactant A and the surfactant B, or the liquid containing the surfactant A and the liquid containing the surfactant B or a mixture of the two liquids has the blood cell elimination effect of the following (2):
(2) preparing a control sample by diluting a predetermined amount of blood with distilled water so that an absorbance value measured by an absorption photometry by use of a micro-plate reader and light of a wavelength of not less than 600 nm is not less than 1 and less than 2; preparing a test sample by use of a liquid containing the surfactant A and the surfactant B, a liquid containing the surfactant A and a liquid containing the surfactant B, or a mixture of these two liquids in place of the distilled water in the control sample, so that the time for the absorbance value of the test sample measured by an absorption photometry by use of light having a wavelength of not less than 600 nm is decreased to a half the absorbance value of the control sample not more than 0.5 hours.

[A14] The method for treating a sample containing blood components according to any one of [A1] to [A13], wherein the method for treating the sample containing blood components is a method of lysing erythrocytes while suppressing degradation in the survival rate of rare cells that may be contained in the sample and/or degrading the survival rate of leukocytes.

[A15] A method for separating or detecting a rare cell or a nucleic acid in a sample containing blood components, the method comprising treating a sample containing blood components by any of the treatment methods according to any one of [A1] to [A14], and separating or detecting the rare cell or the nucleic acid from the treated sample.

[A16] A method for separating or detecting a rare cell or a nucleic acid in a sample containing blood components, comprising separating from a sample containing blood components a fraction containing the rare cell or the nucleic acid, treating the separated fraction by the treatment method according to any one of [A1] to [A14], and separating or detecting the rare cell or the nucleic acid from the treated fraction.

[A17] The method for separating or detecting a rare cell or a nucleic acid in a sample containing blood components according to [A15] or [A16], wherein the separation or the detection of the rare cell or the nucleic acid is carried out by a method selected from the group consisting of separation using affinity, density separation, centrifugation separation, adhesion separation, sizing separation, flow cytometry, electrical separation, magnetic separation, sowing on a medium, and a combination thereof.

[A18] The method for separating or detecting a rare cell or a nucleic acid in a sample containing blood components according to any one of [A15] to [A17], wherein the rare cell is a cell selected from the group consisting of a cancer cell, circular tumor cell, a vascular endothelial cell, a vascular endothelial precursor cell, a cancer stem cell, an epithelial cell, a hematopoietic stem cell, a mesenchymal cell, a fetal cell, and a combination thereof.

[A19] The method for separating or detecting a rare cell or a nucleic acid in a sample containing blood components according to any one of [A15] to [A18], wherein the nucleic acid is a nucleic acid selected from the group consisting of; RNA and DNA in a blood component; RNA and DNA in a cancer cell, circular tumor cell, a vascular endothelial cell, a vascular endothelial precursor cell, a cancer stem cell, an epithelial cell, a hematopoietic stem cell, a mesenchymal cell and a fetal cell; and a combination thereof.

[A20] The method for separating or detecting a rare cell or a nucleic acid in a sample containing blood components according to any one of [A15] to [A19], wherein the rare cell is labeled by use of a labeling method associated with a detection method selected from the group consisting of; a detection method using a radioactive substance, a detection method using a luminous phenomenon, a detection method using a pigment, a detection method using magnetism, an electrical detection method, an optical detection method, and a combination thereof.

[A21] A method for measuring the number of CTCs (circulating tumor cells) or a nucleic acid of a CTC in a sample containing blood components, the method comprising treating a sample containing blood components by the treatment method according to any one of [A1] to [A14], or separating/detecting a rare cell or a nucleic acid from a sample containing blood components by the separation/detection method according to any one of claims [A15] to [A20].

[A22] A method for assaying a rare cell in a sample containing blood components, the method comprising treating a sample containing blood components by the treatment method according to any one of [A1] to [A14], and subsequently assaying by a method comprising an observation of movements of the cell or an activity measurement.

[A23] A reagent kit comprising the surfactant A and the surfactant B to be used for the treatment method according to any one of [A1] to [A14], the separation/detection method according to any one of [A15] to [A20], the CTC number measurement method according to [A21], and/or the assaying method according to [A22].

[A24] A reagent kit comprising the surfactant A to be used for the treatment method according to any one of [A2] to [A14], the separation/detection method according to any one of [A15] to [A20], the CTC number measurement method according to [A21], and/or the assaying method according to [A22].

EXAMPLES

The disclosure will be described below more specifically by referring to the following Examples, though the Examples are not intended to limit the disclosure.

[1. Treatment with Polyoxyethylene Octyl Dodecylether (EO=25)( Examples1, 2]

Prepared was a 2.5 w/v % aqueous solution of polyoxyethylene octyl dodecylether (EO=25) represented by Chemical formula (1) above (trade name: EMULGEN (trade name) 2025G, manufactured by Kao Corporation, Surfactant No. 1 in Table 1 below). The time for lysing erythrocytes at contact with this aqueous solution was measured. Further, the survival rate of leukocytes and the survival rate of cancer cells 10 minutes after (Example 1) or 30 minutes after (Example 2) from the contact with this aqueous solution were measured. Specifically, the measurements were carried out under the conditions as stated below.

[Measurement of Lysis Time of Erythrocytes]

As a sample containing erythrocytes, blood that had been collected from a vein of a healthy person by use of a vacuum blood-collecting vessel (EDTA including 2K) was used. 30 µL of the sample containing the blood was dispensed onto a 96-well microplate, in which 30 µL of the aqueous solution of surfactant was mixed and stirred five times with pipetting, thereby allowing the reaction solution to react homogeneously. The absorbance was measured every one minute with a micro-plate reader. The moment at which the absorbance became 0.5 or lower at a wavelength of 650 nm was determined as the lysis of the blood cells. The results are shown in Table 3 below (Examples 1 and 2). In Examples 1 and 2, the absorbance reached 0.5 within the time period from 30 minutes to 60 minutes after starting the measurement. On the other hand, in Comparative Example 9 where the aqueous solution of the surfactant was replaced by distilled water, the absorbance did never reach 0.5 even 60 minutes after from the start of the measurement. The micro-plate reader used herein was Thermo Labsystems Multiskan Ascent 35 manufactured by Thermo Labsystems.

[Assessment of Damage to Leukocytes]

Leukocytes were separated from 10 ml of fresh blood in accordance with HetaSep protocol (manufactured by STEMCELL (trade name) Technologies), which was suspended in 1 ml of PBS(−) and collected in a 1.5 ml disposable microtube (a microcentrifuge tube with trade name of DSP-MC-15A manufactured by Nichiryo Co., Ltd.). Since a small amount of erythrocytes were still included in the separated leukocytes, the erythrocytes were eliminated by using ammonium chloride (supplied by STEMCELL (trade name) Technologies) in accordance with the attached document, and the leukocytes were collected through centrifugation, washed in PBS(−), and then suspended in 1 ml of a serum-including medium. 50 µL of leukocyte suspension in the serum-including medium and 50 µL of the aqueous solution of the surfactant were mixed in the 1.5 ml microcentrifuge tube, and the mixed solution was stirred with pipetting about five times so that the solution would be homogeneous. Subsequently, the solution was allowed to stand at an ambient temperature of 23° C. for about 10 minutes to about 30 minutes so as to proceed the reaction. Later, the reaction liquid in this microcentrifuge tube was stirred with pipetting so as to disperse the cells and then 50 µL of the liquid was dispensed into another microcentrifuge tube in which 50 µL of 0.4% trypan blue stain solution (manufactured by Invitrogen) was mixed. This was injected into a counting chamber (Cell Counter Plate: Advanced Neubauer type 177-112C manufactured by WATSON Co., Ltd.) so as to count living cells that had not been stained with the trypan blue. Provided that the number of cells in a reaction liquid to which distilled water had been added in place of the reagent being 100%, the survival rate was calculated from the number of cells survived 10 minutes after (Example 1) and 30 minutes after (Example 2) from the reaction with the aqueous solution of surfactant. The results are shown in Table 3 below.

[Assessment of Damage to Cancer Cells]

Cells of SNU-1, MCF-7, SW620, PC3, and NCI-358 derived from gastric cancer, breast cancer, large intestinal cancer, prostate cancer, and lung cancer were prepared to be $2×10^6$ Cells/ml and used. The cancer cells were prepared in the following manner. 50 µL of a cancer cell suspension in the serum-including medium and 50 µL of the aqueous solution of the surfactant were added into the 1.5 ml microcentrifuge tube, stirred with pipetting so as to make the solution homogeneous. Later, the solution was allowed to stand at an ambient temperature of 23° C. for about 10 minutes so as to proceed the reaction. Then, the reaction liquid in the microcentrifuge tube was stirred with pipetting so as to disperse the cells, and subsequently, 50 µL of the liquid was dispensed into another microcentrifuge tube and 50 µL of 0.4% trypan blue stain solution (Invitrogen) was mixed therein. This was injected into a counting chamber so as to count living cells that had not been stained with the trypan blue. Provided that the number of cells in a reaction liquid to which distilled water had been added in place of the reagent being 100%, the survival rate was calculated from the number of cells survived 10 minutes after (Example 1) and 30 minutes after (Example 2) from the reaction with the aqueous solution of the surfactant. The results are shown in Table 3 below.

(Preparation of Cancer Cells)

According to an ordinary method, after eliminating the supernatants, media of human mammary epithelial cancer (cell strain name: MCF-7 supplied by DS Pharma Biomedical Co., Ltd.), human colonic gland cancer (cell strain name: SW620 supplied by DS Pharma Biomedical Co., Ltd.), human prostate cancer (cell strain name: PC3 supplied by DS Pharma Biomedical Co., Ltd.) and human alveolar cell carcinoma (cell strain name: NCI-H358 supplied by DS Pharma Biomedical Co., Ltd.), which had been cultivated on TC Dish (Greiner Bio-one), were washed with PBS(−) in order to further eliminate the supernatants, and then was treated with trypsin (supplied by Invitrogen) at 37° C. for 3 minutes. After adding a serum-including medium thereto, each of the cancer strains was collected in a 15 ml centrifugation tube. This was centrifuged by using a centrifugal machine (CF20F supplied by Hitachi, Ltd.), thereby eliminating the supernatant. This was again suspended in the serum-including medium and collected. A human gastric cancer cell strain (SNU-1: ATCC) as a floating type was collected into a 15 ml centrifugation tube without a trypsin treatment. After centrifugation, a serum-including medium was added before suspending and collecting the cell strain.

As indicated by Examples 1 and 2 in Table 3, the aqueous solution of the surfactant No. 1 (polyoxyethylene octyl dodecylether (EO=25)) can lyse the erythrocytes and lower selectively the survival rate of the leukocytes rather than cancer cells. The effect became remarkable 30 minutes after the contact with the surfactant No. 1.

[2. Treatment Using Combination of Two Kinds of Surfactants(Examples 3-7)]

Using 14 kinds of surfactants (manufactured by Kao Corporation, Nacalai Tesque Inc., Dojindo Molecular Technologies, Inc., and Lion Akzo Co., Ltd.) recited in Table 1 below, mixtures were prepared by setting combinations of Examples 3-7 and Comparative Examples 1-8 shown in Table 3 below. Regarding the surfactant mixtures of Examples 3-7 and Comparative Examples 1-8, the mixing ratio of the two surfactants (weight ratio) was set to 2:8 (i.e., the surfactant No. 1 occupies 80%). The total concentration of the surfactant in each of the surfactant mixtures was set to 2.5 w/v %. Comparative Example 9 indicates an example where distilled water including no surfactant was used. Similarly to Example 1, the time for lysing erythrocytes at the time of contacting with any of these surfactants was measured, so as to measure the survival rate of leukocytes and the survival rate of cancer cells 10 minutes after the contact with the surfactant. The specific conditions were similar to those of Example 1 except that the aqueous solution of surfactant in Example 1 was replaced by the mixture of surfactants. The results are shown in Table 3. Table 2 shows the measurement result for the erythrocyte lysis time of a 2.5 w/v % aqueous solution for a case where each of the surfactants No. 1 to No. 6 was used alone.

TABLE 1

| | | Surfactant | |
|---|---|---|---|
| No. | Reagent name (or trade name) | Hydrophilic part | Hydrophobic group |
| 1 | EMULGEN 2025G | Nonionic surfactant (polyoxyethylene alkyl ether), manufactured by Kao Corporation | Double strands of chain length (C*12,C8) |
| 2 | EMULGEN MS-110 | Nonionic surfactant (polyoxyethylene polyoxypropylene alkyl ether, HLB value = 12.7, cloudy point(° C./2% aqueous solution) = 55), manufactured by Kao Corporation | Chain length (C12) |
| 3 | EMULGEN 2020G-HA | Nonionic surfactant (polyoxyethylene alkyl ether), manufactured by Kao Corporation | Double strands of chain length (C12,C8) |
| 4 | EMULGEN LS-110 | Nonionic surfactant (polyoxyethylene polyoxypropylene alkyl ether, HLB value = 13.4, cloudy point(° C./2% aqueous solution) = 73), manufactured by Kao Corporation | Chain length (C12) |
| 5 | EMUNONE 1112 | Nonionic surfactant (polyoxyethylene fatty acid ester), HLB = 13.7, manufactured by Kao Corporation | Chain length (C12) |
| 6 | Sucrose laurate | Nonionic surfactant (sugar chain), HLB16, manufactured by Dojindo Molecular Technologies, Inc. | Chain length (C12) |
| 7 | NEOPELEX | Anion (sulfate group), manufactured by Kao Corporation | Chain length (C12) + benzene ring |
| 8 | Lauryl sodium carboxylate | Anion (surfactant having carboxylic acid at hydrophilic part), manufactured by Nacalai Tesque Inc. | Chain length (C12) |
| 9 | Lauryltrimethyl ammonium chloride | Cation, manufactured by Nacalai Tesque Inc. | Chain length (C12) |
| 10 | PELEX OP-T | Anion (sulfate group), manufactured by Kao Corporation | Double strands of chain length (C8,C8) |
| 11 | Decyltrimethyl ammonium chloride | Cation, manufactured by Lion Akzo Co., Ltd. | Chain length (C10) |
| 12 | AMPHITOL 20BS | Dipolar ion, manufactured by Kao Corporation | Chain length (C12) |
| 13 | AMPHITOL 20N | Dipolar ion, manufactured by Kao Corporation | Chain length (C12) |
| 14 | AMPHITOL 20YB | Dipolar ion, manufactured by Kao Corporation | Chain length (C12) |

*The number after 'C' denotes the carbon number.

TABLE 2

| No. | Surfactant (reagent name or trade name) | Preparation concentration w/v % | Lysis time to reach absorbance of 0.5 (min) |
|---|---|---|---|
| 1 | 2025G | 2.5 | 30-60 |
| 2 | MS-110 | 2.5 | 1 |
| 3 | 2020HA | 2.5 | 2 |
| 4 | LS-110 | 2.5 | 1 |
| 5 | EMUNONE | 2.5 | 2 |
| 6 | Sucrose laurate | 2.5 | 1 |
| — | Water | — | Not achieved |

TABLE 3

| | Surfactant | | Lysis time to reach absorbance of 0.5 (min) | Leukocyte survival rate (%) | Cancer cell survival rate (%) (10 minutes after a contact with surfactant) | | | | |
|---|---|---|---|---|---|---|---|---|---|
| | (2.5 w/v %) mixing ratio 2:8 | | | | SNU-1 Gastric cancer | MCF-7 Breast cancer | SW620 Large intestinal cancer | PC3-9 Prostate cancer | MCI-358 Lung cancer |
| | No. | No. | | | | | | | |
| Ex. 1 | 1 | 1 | 30-60 | 71.8 | 86.1 | 112.3 | 81 | 101.8 | 89.9 |
| Ex. 2 | | | | 10.5* | 60.9* | 70.8* | — | — | — |
| Ex. 3 | 2 | 1 | 9 | 37 | 93.7 | 86.2 | 85.28 | 106.9 | 85.1 |
| Ex. 4 | 3 | 1 | 8 | 25.6 | 84.5 | 101.4 | 92.64 | 18.9 | 78.3 |
| Ex. 5 | 4 | 1 | 6 | 7.7 | 60.5 | 65.0 | 5 | 8.0 | 37.8 |
| Ex. 6 | 5 | 1 | 6 | 5.1 | 0.8 | 22.2 | 0 | 67.6 | 14.9 |
| Ex. 7 | 6 | 1 | 29 | 88.5 | 5.5 | 86.2 | 108 | — | 55.7 |
| Co. Ex. 1 | 7 | 1 | 2 | 0 | 0.0 | 0 | 0 | 0.0 | 0 |
| Co. Ex. 2 | 8 | 1 | 4 | 0.0 | 0.0 | 0.0 | — | 4.9 | 0.0 |
| Co. Ex. 3 | 9 | 1 | 2 | 0 | 0.0 | 0.0 | 0 | 0.0 | 0.0 |
| Co. Ex. 4 | 10 | 1 | 2 | 0 | 0.0 | 0 | 0 | 0.0 | 0 |
| Co. Ex. 5 | 11 | 1 | 14 | 0 | 0.4 | 0.0 | 0 | 0.0 | 0.0 |
| Co. Ex. 6 | 12 | 1 | 4 | 1.3 | 1.3 | 0.0 | 0 | 0.0 | 0.5 |
| Co. Ex. 7 | 13 | 1 | 5 | 3.8 | 0.0 | 0.0 | 0 | 0.0 | 0.0 |
| Co. Ex. 8 | 14 | 1 | 27 | 50.0 | 7.1 | 53.2 | 20 | 5.1 | 14.4 |
| Co. Ex. 9 | Distilled water | | (Not achieved) | 100 | 100.0 | 100 | 100 | 100.0 | 100 |

Note:
Ex.: Example, Co. Ex.: Comparative Example
Example 2 refers to a result of measurement 30 minutes after a contact with surfactant.
"—" indicates that no measurement was carried out.

As shown in Table 3, in Examples 1 and 2 where the nonionic surfactant No. 1 is used alone, lysis of the erythrocytes was achieved. Furthermore, in comparison with Comparative Examples 1-8, the survival rate of cancer cells was kept high. In Examples 3-7 where the treatment was carried out with the mixture of surfactants No. 1 and any of Nos. 2-6, the time for lysis of erythrocytes was shortened in comparison with Example 1, and a survival rate was kept high for at least one kind of the cancer cells in comparison with Comparative Examples 1-8. From the viewpoint of lowering the survival rate of leukocytes for the equal time period (10 minutes), Examples 3-6 using respectively the surfactants Nos. 2-5 were superior to Examples 1 and 7. From the viewpoint of keeping the survival rate high for more kinds of cancer cells, Examples 2-5 and 7 are superior to Example 6. Among them, Examples 3, 4 and 7, in particular, Examples 3 and 4 were favorable.

[3. Relationship Between Mixing Ratio of Two Kinds of Surfactants and Damage to Cancer Cell]

A mixture of the surfactant No. 1 and either the surfactant No. 2 or No. 3 was prepared at a mixing ratio of 10:0 to 0:10 (weight ratio: the total concentration of the surfactants was 2.5 w/v %). These mixtures were used for assessing the damage to gastric cancer cells (SNU-1). The damage assessment was carried out as mentioned above. Namely, 50 µL of a cancer cell suspension in the serum-including medium ($2 \times 10^6$ Cells/ml) and 50 µL of the mixture were mixed in a 1.5 ml microcentrifuge tube, stirred with pipetting about five times so as to make the solution homogeneous. Later, the solution was allowed to stand and react at an ambient temperature of 23° C. for about 10 minutes. Then, the reaction liquid in the microcentrifuge tube was stirred with pipetting so as to disperse the cells, and subsequently, 50 µL of the liquid was dispensed into another 1.5 ml microcentrifuge tube and mixed with 50 µL of 0.4% trypan blue stain solution (supplied by Invitrogen). This was injected into a counting chamber so as to count living cells that had not been stained by the trypan blue, using an inverted microscope (supplied by Olympus Corporation). The survival rate was calculated from the number of cells survived after the reaction with the mixture of surfactants, provided that the number of cells in a reaction liquid to which distilled water had been added in place of the reagent being 100%. The results with regard to the mixture the surfactant No. 2 and the surfactant No. 1 are shown in FIG. 1 and the results with regard to the mixture the surfactant No. 3 and the surfactant No. 1 are shown in FIG. 2.

Figure 1:
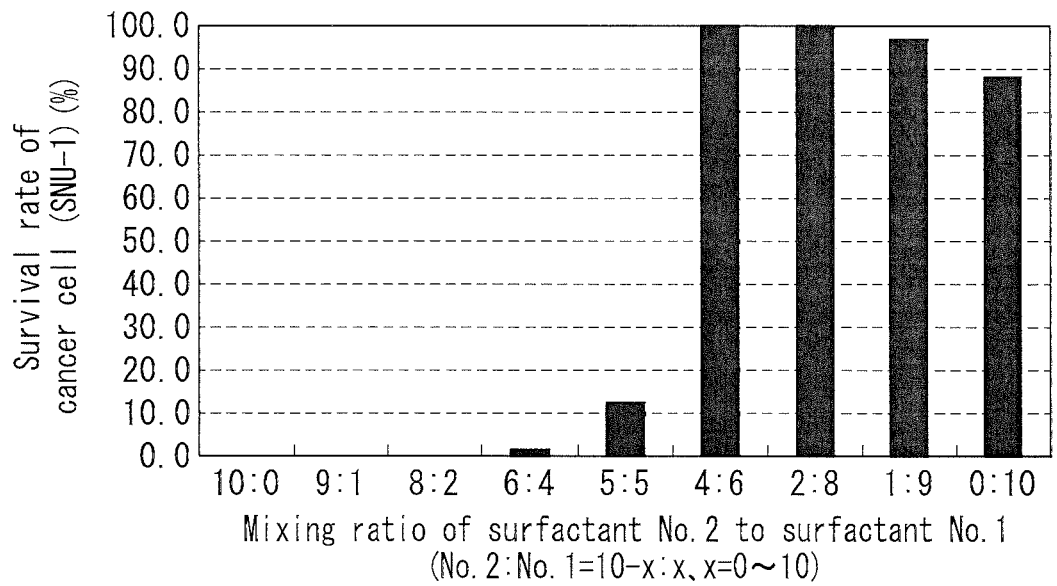
FIG. 1 is a graph showing the relationship between a mixing ratio of a surfactant No. 2 to a surfactant No. 1 and a survival rate of cancer cells.
Figure 2:
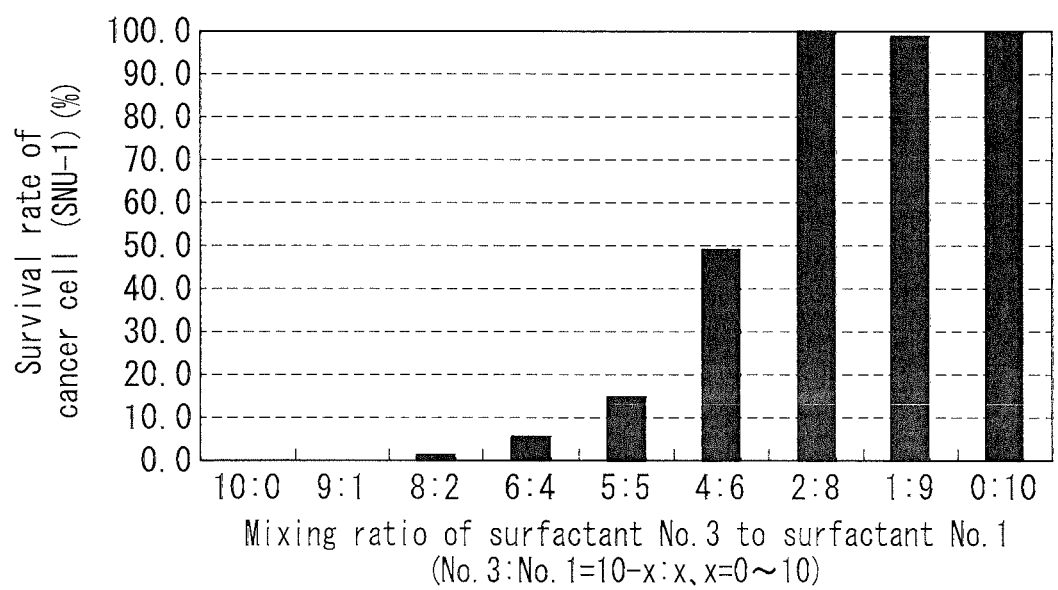
FIG. 2 is a graph showing the relationship between a mixing ratio of a surfactant No. 3 to a surfactant No. 1 and a survival rate of cancer cells.

As shown in FIGS. 1 and 2, in a case where the mixing ratio of each of the surfactant No. 2 and No. 3 (weight ratio) exceeded 50%, the survival rate of cancer cells was degraded considerably. In a case where the mixing ratio of the surfactant No. 1 (weight ratio) exceeded 50%, the survival rate of cancer cells was raised considerably. In a case where the mixing ratio of the surfactant No. 1 (weight ratio) was 60% or higher, the improvement of the survival rate of cancer cells was remarkable.

[4. Adhesion and Separation of Cancer Cells from a Sample Containing Blood Containing a Cancer Cell]

The cell surface of MCF-7 cell as a breast cancer cell was washed with PBS(−) (Dulbecco's PBS(−) manufactured by Nissui Pharmaceutical Co., Ltd.) and then the cell was peeled off by trypsinization (37° C., 3 minutes), and suspended in a serum-including medium. The cells were counted with a counting chamber, and $1 \times 10^6$ of cells were introduced into each centrifugal tube for centrifugation, from which supernatants were eliminated and to which 1 ml of blood was added and suspended so as to prepare a sample containing blood containing a cancer cell. Into this 1 ml of a sample containing blood containing a cancer cell, 1 ml of surfactant mixture of either Example 3 or 4 (mixture of the surfactant No. 1 with either the surfactant No. 2 or the surfactant No. 3; the total concentration was 2.5 w/v %) was mixed, stirred five times with pipetting, and allowed to react for 10 minutes.

Figure 3:
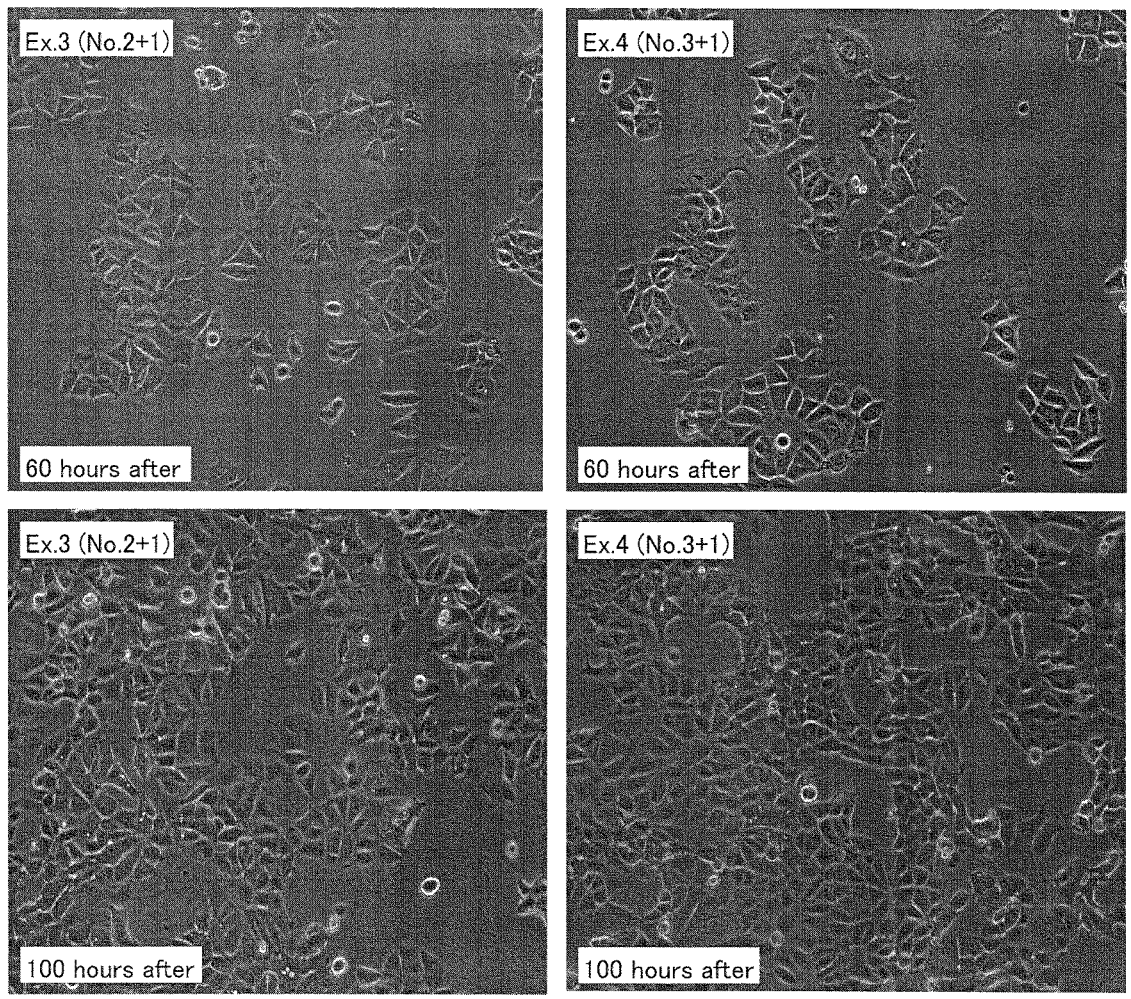
FIG. 3 is composed of microscopic photographs showing the result of cultivating cancer cells collected by centrifugation separation after the treatment with a surfactant mixture.

The blood cells are lysed during the reaction and the density of the reaction solution is increased. For this reason, at the time of centrifugation separation of the cells, an appropriate amount of buffer is added to lower the density. Specifically, 10 ml of reactant and the buffer were introduced into a centrifugal tube and subjected to centrifugation for 3 minutes at 1500 rpm and at ambient temperature (24° C.) in a centrifugal machine (CR20F manufactured by Hitachi, Ltd.). After eliminating the supernatant, the reactant is suspended in a medium including 10 ml of serum, the cells are sown on a 10 cm TC Dish (Greiner Bio-one) and kept in a 5% $CO_2$ incubator at 37° C. After 24 hours, the medium was exchanged, and the cells were kept again in the incubator. FIG. 3 includes photographs showing the growing conditions 60 hours after and 100 hours after. As shown in FIG. 3, cancer cells were collected from the samples containing blood containing a cancer cell by use of the surfactant mixture of Example 3 or 4, and the cancer cells adhered to the cultivation dish and proliferated. Namely, it was possible to further separate and/or concentrate the cancer cells after the reaction treatment and centrifugal separation. In a case where the cells were sown without the above-mentioned reaction treatment, the blood components such as blood cells and blood platelets hindered the cancer cells from adhering and growing.

[5. Filtering of Blood Sample Containing Fluorescent Stained Cancer Cell]

Cancer cells that had been fluorescent stained were mixed with blood so as to prepare a blood sample containing a cancer cell. This was treated with a surfactant mixture, and filtered so as to observe the cells collected on the filter. Specific procedures are described below.

[Blood Sample Containing a Cancer Cell]

As a sample containing blood containing a cancer cell, 1 ml of blood to which about 6000 cells of gastric cancer (SNU-1) stained previously in the following manner was prepared.

(Staining of Cancer Cell)

The cancer cells (SNU-1) prepared similarly to the above [1.] were collected from the culture solution, and then subjected to centrifugation for 3 minutes in a centrifugal machine (CR20F manufactured by Hitachi, Ltd.) at 1500 rpm at ambient temperature (24° C.). After removing the supernatant, PBS(−) was added to suspend the cells. The cells suspended in the PBS(−) were fluorescent-stained. For the staining reagent, CellTracker (Invitrogen) was used. The CellTracker is a reagent that can pass through even the cell membrane of a living cell, and thus it reacts with the intracellular substance and is transformed to a fluorescent substance. The CellTracker was dissolved to be 10 mM in DMSO and used such that the final concentration at the reaction would be in the range of 0.5 to 0.25 μM. It was allowed to react in the PBS(−) for 30 to 40 minutes. The cancer cells (SNU-1) were stained with CellTracker Green (CMFDA/C7025) that emits green fluorescence.

[Surfactant Mixture]

As the surfactant mixture, the surfactant mixture of Example 4 (mixture of surfactant No. 3 and surfactant No. 1: the total concentration of the surfactants was 2.5 w/v %) was prepared.

[Filter]

Nuclepore Track Etch Membrane of Φ13 mm and having a pore size of 8 μm (supplied by GE Healthcare) was fixed with a Swinnex Filter Holder (SX0001300 supplied by Yamato Scientific Co., Ltd.), thereby forming a filter. A plastic syringe from which a piston had been detached was attached to the upper part of the filter holder. The lower part of the filter was connected with a silicone tube, and the top end of the other side was fixed inside a liquid waste bottle, thereby the filter was used.

[Filtration]

In 1 ml of the sample containing the blood containing a cancer cell, 1 ml of the surfactant mixture of Example 2 was mixed, stirred five times with pipetting and allowed to react for 10 minutes. The reactant was added to a syringe connected to the upper part of the filter for filtration. Subsequently, a PBS(−) solution was added quietly before the blood passing through the filter entirely, thereby washing the filter. Later, fixation was carried out for about 30 minutes with a 4% paraformaldehyde/PBS buffer solution (Wako Pure Chemical Industries Ltd.). The cells fixed on the membrane of the filter were observed with a microscope. The results are shown in FIG. 4B. FIG. 4A shows the results of a case where blood was filtered without any treatment by use of such a surfactant mixture.

In FIG. 4B showing a case where treatment with a surfactant mixture was carried out, substantially no blood cells are observed while many blood cells are observed in FIG. 4A. The dots in FIG. 4B are pores of the filter. The shining cells in FIG. 4B are cancer cells stained and mixed in the blood previously. It can be observed that even after a reaction with the surfactant, the blood cells are destroyed and the cancer cells are captured on the filter. This result shows that the purity of cancer cells residing on the filter is increased and thus detection and the subsequent analysis will be carried out easily.

The above data indicate that because of the treatment with the surfactant mixture, the blood cells and the like are destroyed while the rare cells (cancer cells) in the sample containing the blood is imposed less damage, and thus it is possible to carry out adhesion separation and cultivation with high purity, filter separation, fluorescent labeling and the like. As a result, a precise assay of the collected rare cells (cancer cells) will be possible.

[6. Noise Elimination in Visualization of Cancer Cell in a Blood Sample Containing a Cancer Cell]

A sample was prepared by mixing cancer cells that had been fluorescent-stained and leukocytes that had been stained. After a treatment with a surfactant mixture, the sample was observed with a fluorescence microscope. Specifically, the sample was prepared under the conditions as mentioned below.

[Preparation of a Blood Sample Containing a Cancer Cell]

Similarly to the above [5.], cancer cells (SNU-1) were prepared by staining with CellTracker Green CMFDA/C7025 that emits green fluorescence, and leukocytes were prepared by staining with CellTracker Blue CMF2HC/C12881 that emits blue fluorescence. 200 μL of serum-including medium including 6700 cancer cells and $1.4 \times 10^6$ of leukocytes was introduced into a microcentrifuge tube, thereby preparing a blood sample containing a cancer cell. This was dispensed into other microcentrifuge tubes so that the content each would be 30 μL.

[Treatment with Surfactant Mixture and Observation with Fluorescence Microscope]

The blood sample containing a cancer cell was treated under the conditions as illustrated in Table 4 below (Examples 8-10 and Comparative Example 10). The concentrations recited in the table are the concentration during the preparation. At the time of reaction with a cell suspension, equivalent 30 μL was added and mixed. The reaction temperature was the ambient temperature of 23° C. After the reaction, 640 μL of medium was added, and centrifugation was carried out for 3 minutes at 2500 rpm with a centrifugal machine (CF15D manufacture by Hitachi, Ltd.). It was suspended again in 600 μl of PBS(−) and then centrifuged again by using the same centrifugal machine under the same conditions. Subsequently, it was suspended in 100 μl of PBS(−), 50 μl of which was dispensed onto a 384 plate. This was centrifuged for 5 minutes at 400×g with a plate centrifugal machine (M20484A000) supplied by Kubota Corporation, and observed with a fluorescence microscope under the conditions as illustrated in Table 5 below. FIG. 5 shows the results of fluorescence microscope observation. Table 4 shows the results of counting the number of cells in FIG. 5.

TABLE 4

| | | | Microscopic observation result | | | |
|---|---|---|---|---|---|---|
| | Surfactant | Content | Reaction time (min) | SNU-1 (pieces) | SNU-1 (%) | Leukocyte (pieces) | Leukocyte (%) |
| Ex. 8 | No. 2 + No. 1 (No. 2:No. 1 = 2:8) | 2.5 w/v % | 10 | 40 | 69.0 | 57 | 0.76 |
| Ex. 9 | No. 3 + No. 1 (No. 3:No. 1 = 2:8) | 2.5 w/v % | 10 | 31 | 53.4 | 187 | 2.50 |
| Ex. 10 | No. 1 | 5.0 w/v % | 30 | 35 | 60.3 | 291 | 3.88 |
| Co. Ex. 10 | Distilled water | — | 10 | 58 | 100 | 7491 | 100 |

TABLE 5

<Condition>
Object lens: 10x
Blue excitation-green observation
UV excitation-blue observation

| | EX (excitation) | DM | BA (fluorescence) |
|---|---|---|---|
| UV set | 365/±10 | 400 or more | 470/±20 |
| B set | 475/±15 | 505 or more | 525/±10 |
| Exposure time | SNU-1 labeling 24 msec Leukocyte labeling 64 msec | | |

As shown in FIG. 5 and Table 4, in Examples 8-10, the number of leukocytes was decreased considerably after the treatment, and the noise in the microscopic observation was decreased remarkably in comparison with Comparative Example 10.

[7. Detection and Separation by Flow Cytometry]

Here, leukocytes isolated from 10 ml of blood similarly to the above [1.] were used. For the cancer cells, SNU-1 cells were used. For measurement, an automated cell counter MoxiZ by ORFLO, which uses the electrical sensing zone method (Coulter Principle) was used. The electrical sensing zone method is a method including flowing electric current through apertures, and measuring and detecting as a change in the voltage pulse or the like the change in the electrical resistance in proportion to the volume of particles passing through the apertures. Volume distribution histogram is obtained by counting and processing the voltage pulse height one by one. Thereby the size (volume) and number of the cells can be measured.

A mixture of the surfactant No. 2 and the surfactant No. 1 at a mixing ratio of 2:8 (weight ratio, the total concentration of the surfactant was 2.5 w/v %) was prepared. By using the surfactant mixture, particle size distribution of gastric cancer cells (SNU-1) and that of leukocytes were measured. 50 μL of a cancer cell suspension ($1\times10^5$ Cells/ml) or leukocytes ($3\times10^5$ Cells/ml) in a serum-including medium and 50 μL of the surfactant mixture were mixed in a 1.5 ml microcentrifuge tube, stirred about five times with pipetting so as to make the solution homogeneous. Later, the solution was allowed to stand at an ambient temperature of 23° C. for about 10 minutes so as to proceed the reaction. After the reaction, the reaction solution in the microcentrifuge tube was stirred with pipetting so as to disperse the cells, and 75 μL thereof was poured into a special cassette for MoxiZ, thereby measuring the particle size distribution (Example 11). In a comparative example, distilled water was used in place of the surfactant mixture (Comparative Example 11).

Next, the cancer cells and the leukocytes were mixed to prepare a cell sample so that the number of cells would be equal to the number of the above-mentioned number of the cells. The cell sample was allowed to react with the surfactant mixture and the particle size distribution was measured similarly to Example 11 (Example 12). In a comparative example, distilled water was used in place of the surfactant mixture (Comparative Example 12).

The data obtained after the measurement can be outputted as a CSV file. Smoothing was carried out by a 7-point simple moving average regarding the data obtained for the respective sizes. FIGS. 6A and 6B each shows a result obtained by superimposing data of the respective particle size distributions of cancer cells and leukocytes. FIGS. 7A and 7B show particle size distributions of suspensions of a mixture of the cancer cells and leukocytes.

As shown in FIG. 6A, FIG. 6B, FIG. 7A, and FIG. 7B, in Comparative Examples 11 and 12 (FIGS. 6B and 7B), the particle size distribution of the larger particles of leukocytes and the particle size distribution of the smaller particles of the cancer cells are overlapped with each other in the cell counter ("overlapped area" in FIG. 6B, and FIG. 7B). As a result, it is difficult to isolate and divide the leukocytes and SNU-1, and many leukocytes will be mixed in the collected SNU-1. On the other hand, in Example 11 (FIGS. 6A and 7A), the leukocytes in the overlapped area are lysed, and thus there exists no or a small overlapped area. As the overlapped area disappears or decreases, purity of the cancer cells is improved. For example, by collecting the cells indicated with a dotted line (5.5 (au)), which has a size of lysed leukocyte or larger, the distribution of the leukocytes and the distribution of the cancer cells can be separated. In this way, it is possible to decide the particle size electrically so as to separate and detect cells of any arbitrary size. Further, detection and separation become possible optically by use of fluorescent labeling and scattered light.

[8. Effect of pH of Surfactant Mixture on Cancer Cells and Leukocytes Suspended in a Physiological Solution]

A surfactant mixture containing the surfactant No. 2 and the surfactant No. 1 at a mixing ratio of 2:8 (weight ratio; the total concentration of the surfactant is 2.5 w/v %) was prepared by using each PBS(−) solution so that the pH would be in a range of 4 to 10. A damage assessment with respect to gastric cancer cells (SNU-1) was carried out by using these surfactant mixtures.

The damage assessment was carried out as mentioned above except that the cells were suspended not in a serum-including medium but in a physiological saline. Namely, 50 μL of a cancer cell suspension of the physiological saline ($2\times10^6$ Cells/ml) and 50 μL of the mixture were mixed in a 1.5 ml microcentrifuge tube, stirred with pipetting about five times so as to make the solution homogeneous. Later, the solution was allowed to stand and react at an ambient temperature of 23° C. for about 10 minutes. Then, the reaction liquid in the microcentrifuge tube was stirred with pipetting so as to disperse the cells, and subsequently, 50 μL of the liquid was dispensed into another 1.5 ml microcentrifuge tube and mixed with 50 μL of 0.4% trypan blue stain solution (supplied by Invitrogen). This was injected into a counting chamber so as to count living cells that had not been stained by the trypan blue, using an inverted microscope (supplied by Olympus Corporation). The survival rate was calculated from the number of cells survived after the reaction with the surfactant mixtures, provided that the number of cells in a reaction liquid to which PBS(-) including no surfactant had been added in place of the reagent being 100%.

Similarly, leukocytes were suspended in a physiological saline ($8.2\times10^6$ Cells/ml) and allowed to react. The survival rate was calculated from the number of cells survived after the reaction with the surfactant mixtures, provided that the number of cells in a reaction liquid to which PBS( ) including no surfactant had been added in place of the surfactant mixture being 100%.

The results are shown in FIG. 8 and Table 6 below. As shown in FIG. 8 and Table 6, from the viewpoint of raising the survival rate of the cancer cells and lowering the survival rate of leukocytes, it is preferable that the pH of the surfactant mixture is closer to neutral.

TABLE 6

| pH | Survival rate (%) | | | | |
|---|---|---|---|---|---|
| | pH 4.0 | pH 6.0 | pH 7.4 | pH 8.4 | pH 10 |
| SNU-1 | 38.6 | 93.4 | 96.3 | 51.7 | 50.9 |
| Leukocyte | 0 | 4.9 | 4.9 | 7.3 | 7.3 |

INDUSTRIAL APPLICABILITY

The disclosure is useful in the field of collection, measurement and assay of rare cells in blood, for example, in the scientific fields such as medicine and pharmacy, and/or medical fields such as diagnosis and therapy.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A method for separating or detecting a tumor cell and/or a cancer cell in a sample containing blood components, the method comprising treating the sample by mixing the sample with a liquid containing a surfactant A, wherein no fixation agent is used, and the surfactant A is a nonionic surfactant represented by formula (I)

$$R^1\text{—O-(EO)}_n\text{-}R^2 \qquad (I)$$

wherein:
 $R^1$ is a hydrocarbon group having a branched chain and having a carbon number in the range of 12 to 40,
 EO is an oxyethylene group,
 n is an average addition mole number of EO in the range of 23 to 50, and
 $R^2$ is a hydrogen atom or a hydrocarbon group having a carbon number in the range of 1 to 3,
 wherein the method eliminates erythrocytes and leukocytes present in the sample while suppressing damage to the tumor cell and/or the cancer cell.

2. The method according to claim 1, wherein the surfactant A is a polyoxyethylene alkylene ether with an EO in a range of 23 to 35.

3. The method according to claim 1, wherein the liquid containing the surfactant A satisfies a blood cell elimination effect as described in (1) below:
 (1) preparing a control sample by diluting a predetermined amount of blood with distilled water so that an absorbance value measured by absorption photometry using a micro-plate reader and light of a wavelength of not less than 600 nm is not less than 1 and is less than 2; and
 preparing a test sample from a liquid containing 2.5 to 5 w/v % of the surfactant A, so that the time for the absorbance value of the test sample measured by absorption photometry by light having a wavelength of not less than 600 nm to be decreased to half of the absorbance value of the control sample is not more than one hour.

* * * * *